US011844558B2

(12) United States Patent
Lazarus et al.

(10) Patent No.: US 11,844,558 B2
(45) Date of Patent: Dec. 19, 2023

(54) METHODS FOR TREATING EATING DISORDERS IN PATIENTS VIA RENAL NEUROMODULATION

(71) Applicant: Medtronic Ireland Manufacturing Unlimited Company, Dublin (IE)

(72) Inventors: Gabriel Lazarus, Santa Rosa, CA (US); Douglas A. Hettrick, Andover, MN (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 0 days.

(21) Appl. No.: 17/815,509

(22) Filed: Jul. 27, 2022

(65) Prior Publication Data

US 2022/0370112 A1    Nov. 24, 2022

Related U.S. Application Data

(63) Continuation of application No. 16/456,255, filed on Jun. 28, 2019, now Pat. No. 11,413,084.
(Continued)

(51) Int. Cl.
*A61B 18/00* (2006.01)
*A61F 7/12* (2006.01)
(Continued)

(52) U.S. Cl.
CPC .............. *A61B 18/00* (2013.01); *A61F 7/12* (2013.01); *G16H 20/40* (2018.01); *G16H 20/60* (2018.01);
(Continued)

(58) Field of Classification Search
CPC ........ A61B 18/00; A61B 2017/320069; A61B 18/1492; A61B 2018/00434; A61B 2018/00511; A61B 2018/00577; A61B 2018/0212; G16H 20/40; G16H 20/60; A61F 7/12; A61F 2007/126

See application file for complete search history.

(56) References Cited

U.S. PATENT DOCUMENTS 5,263,480 A * 11/1993 Wernicke ........... A61N 1/36007
607/133
7,499,752 B2 * 3/2009 Maschino .......... A61N 1/36082
607/40

(Continued)

FOREIGN PATENT DOCUMENTS

WO    WO-2018081826 A1 * 5/2018 ......... A61B 5/04001

OTHER PUBLICATIONS

"Sata et al., Role of the Sympathetic Nervous System and its Modulation in Renal Hypertension, Mar. 29, 2018, frontiers in Medicine" (Year: 2018).*

*Primary Examiner* — Carl H Layno
*Assistant Examiner* — Aya Ziad Bakkar
(74) *Attorney, Agent, or Firm* — Shumaker & Sieffert, P.A.

(57) ABSTRACT

Methods for treating eating disorders and for reducing a risk associated with developing an eating disorder in patients via therapeutic renal neuromodulation and associated systems. Renal sympathetic nerve activity can be attenuated to improve a patient's eating disorder status or risk of developing an eating disorder. The attenuation can be achieved, for example, using an intravascularly positioned catheter carrying a therapeutic assembly configured to modulate the renal sympathetic nerve.

20 Claims, 11 Drawing Sheets

Related U.S. Application Data

(60) Provisional application No. 62/693,906, filed on Jul. 3, 2018.

(51) Int. Cl.
*G16H 20/60* (2018.01)
*A61B 17/32* (2006.01)
*G16H 20/40* (2018.01)
A61B 18/02 (2006.01)
A61B 18/14 (2006.01)

(52) U.S. Cl.
CPC ............... *A61B 18/1492* (2013.01); *A61B 2017/320069* (2017.08); *A61B 2018/00434* (2013.01); *A61B 2018/00511* (2013.01); *A61B 2018/00577* (2013.01); *A61B 2018/0212* (2013.01); *A61F 2007/126* (2013.01)

(56) References Cited

U.S. PATENT DOCUMENTS

| | | | | |
|---|---|---|---|---|
| 2015/0051594 | A1* | 2/2015 | Sobotka | A61B 18/04 606/41 |
| 2015/0374437 | A1* | 12/2015 | Sobotka | A61N 5/00 606/41 |
| 2017/0348049 | A1* | 12/2017 | Vrba | A61B 18/1492 |

* cited by examiner

*Arterial Vasculature*

*Venous Vasculature*

Renal Denervation Preclinical Efficacy:
Review of 66 Treated and 64 Naïve Swine

| Group N=Arteries or kidneys | % Non-functional Area | Cortical Axon Area per mm$^2$ | Mean NE (pg/mg) |
|---|---|---|---|
| Naïve 7 day N=64 | 14.6 ± 8.0 | 207.2 ± 134.6 | 264.8 ± 82.9 |
| Symplicity 7 day N=54 | 56.9 ± 28.3 | 66.8 ± 84.6 (68% Decrease) | 92.7 ± 92.7 (65% Decrease) |
| Spyral 7 Day N=12 | 47.3 ± 26.5 | 97.4 ± 73.1 (54% Decrease) | 88 ± 75 (68% Decrease) |

FIG. 8A

| The following questions are concerned with the past four weeks (28 days) only. Please read each question carefully. Please answer all of the questions. Please only choose one answer for each question. | | | | | | | |
|---|---|---|---|---|---|---|---|
| On how many of the past 28 days ...... | No Days | 1-5 days | 6-12 days | 13-15 days | 16-22 days | 23-27 days | Every day |
| 1. Have you been deliberately trying to limit the amount of food you eat to influence your shape or weight (whether or not you have succeeded)? | | | | | | | x |
| 2. Have you gone for long periods of time (8 waking hours or more) without eating anything at all in order to influence your shape or weight? | | x | | | | | |
| 3. Have you tried to exclude from your diet any foods that you like in order to influence your shape or weight (whether or not you have succeeded)? | | | | | x | | |
| 4. Have you tried to follow definite rules regarding your eating (for example, a calorie limit) in order to influence your shape or weight (whether or not you have succeeded)? | x | | | | | | |
| 5. Have you had a definite desire to have an empty stomach with the aim of influencing your shape or weight? | | | | | | | x |
| 6. Have you had a definite desire to have a totally flat stomach? | | | | | x | | |
| 7. Has thinking about food, eating or calories made it very difficult to concentrate on things you are interested in (for example, working, following a conversation, or reading)? | | | | | | x | |
| 8. Has thinking about shape or weight made it very difficult to concentrate on things you are interested in (for example, working, following a conversation, or reading)? | | | | x | | | |
| 9. Have you had a definite fear of losing control over eating? | | x | | | | | |
| 10. Have you had a definite fear that you might gain weight? | x | | | | | | |
| 11. Have you felt fat? | | x | | | | | |
| 12. Have you had a strong desire to lose weight? | | | | | x | | |

| Total Score | 35 | Score>25 → Eating Disorder |
|---|---|---|

FIG. 9

| Answer the questions below by placing "y" or "n" in the box | |
|---|---|
| SDNN (Standard Deviation NN intervals) < 50 ms | y |
| Baroreceptor Sensitivity (BRS) < 1.74 ms/mmHg | y |
| Heart Rate increase > 10 bpm during Stroop Color Test | n |
| Heart Rate increase > 10 bpm or Systolic Blood Pressure increase > 10 mmHg during Stroop Color Test | n |
| Heart Rate increase > 10 bpm or Systolic Blood Pressure increase > 10 mmHg during Cold Pressor Test | n |
| Muscle Sympathetic Nerve Activity > 25 bursts/min | n |

RDN Candidate

FIG. 9 (Cont.)

METHODS FOR TREATING EATING DISORDERS IN PATIENTS VIA RENAL NEUROMODULATION

CROSS-REFERENCE TO RELATED APPLICATION(S)

The present application is a continuation of U.S. patent application Ser. No. 16/456,255, filed Jun. 28, 2019, and entitled, "METHODS FOR TREATING EATING DISORDERS IN PATIENTS VIA RENAL NEUROMODULATION", now U.S. Pat. No. 11,413,084, which claims the benefit of and priority to U.S. Provisional Patent Application No. 62/693,906, filed Jul. 3, 2018, each of which is incorporated herein by reference in its entirety.

TECHNICAL FIELD

The present technology relates generally to systems, devices, and methods for treating eating disorders and/or for reducing a risk associated with developing an eating disorder in patients via renal neuromodulation.

BACKGROUND

An eating disorder is a mental condition characterized by abnormal eating habits that negatively affect a person's physical or mental health. For some eating disorders, obsession with food, body weight, and body shape can cause significant disruption to a person's quality of life, and depending on the severity or the type of eating disorder, the number of symptoms and/or persistence (e.g., duration) of symptoms, these disorders can interfere with mental, physical and/or social function in the affected person, thereby greatly impacting quality of life. In the most severe cases, eating disorders can be life-threatening. The prevalence of anorexia nervosa, bulimia nervosa and binge-eating disorder among adults in the United States is estimated to be about 1.2%, 2%, 5.5%, respectively, with women being much more likely than men to be afflicted with an eating disorder. Further estimates suggest that 1 in 8 young women (e.g., under 20 years) develop some form of diagnosable eating disorder. In addition to physical and mental health impacts, eating disorders also have significant economic burden attributable to work absences and reduced productivity, as well as direct health care costs to patients.

Eating disorders are typically treated with psychotherapy (e.g., cognitive behavior therapy), physical intervention and, in some situations, with medication. Despite current treatment options, however, the burden of eating disorders and other related mental health conditions remains high. As eating disorders can have severe psychological, cognitive, physical, social and economic impact on patients as well as families and society, there is a need for treatments that effectively treat and/or manage eating-related disorders, including the severity of symptoms associated with such disorders. Furthermore, there is a need for treatments that effectively reduce the incidence or development of an eating disorder, or provide other improvements in prognosis and outcomes for patients having, or at risk of developing, an eating-related disorder.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 8A is a display table illustrating results from a study to determine the effects of renal denervation on cortical axon density and mean norepinephrine concentration in animal subjects.

FIG. 9 illustrates an eating disorder risk score calculator for determining a patient's eating disorder risk score in accordance with an embodiment of the present technology.

DETAILED DESCRIPTION

Figure 1:
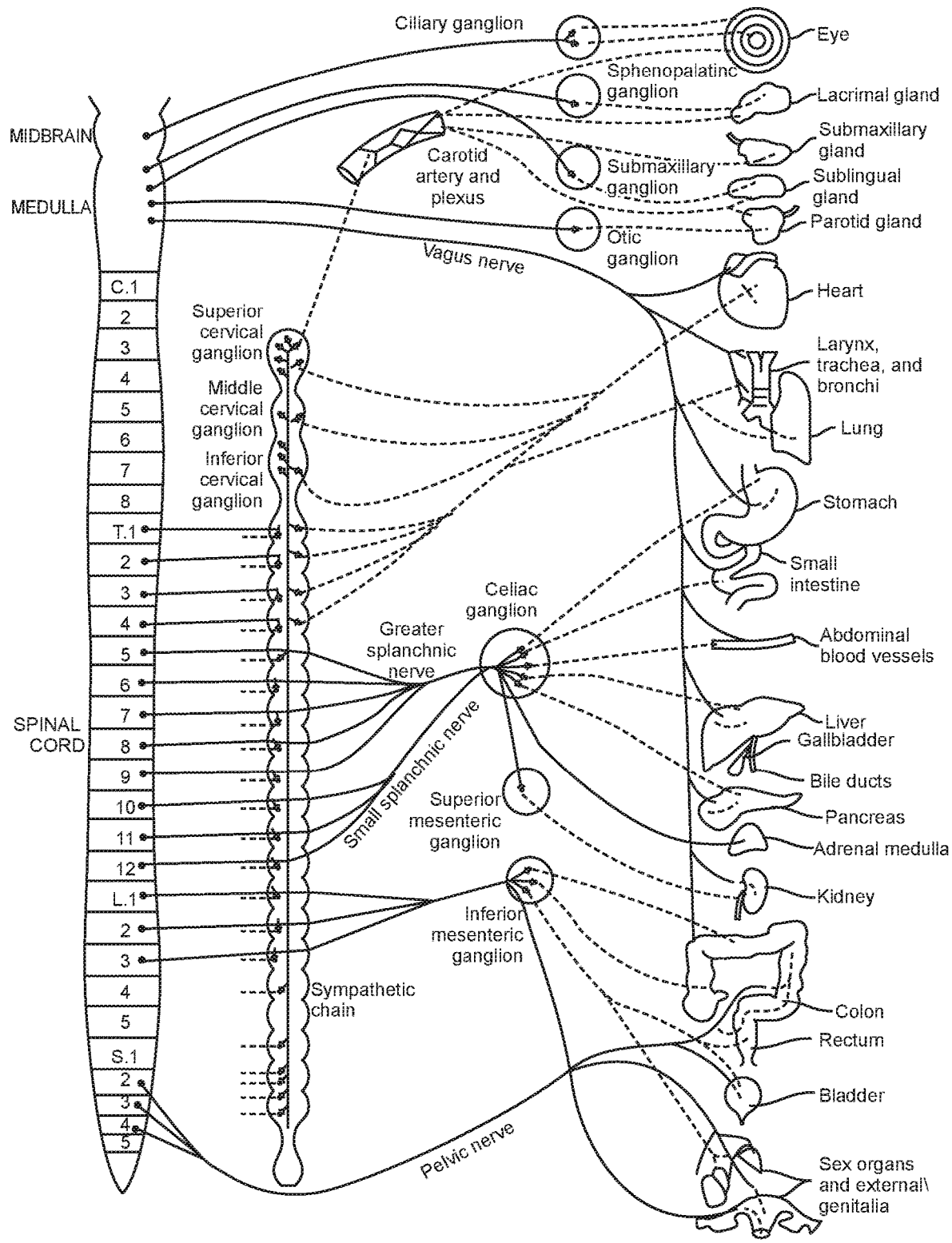
FIG. 1 is a conceptual illustration of the sympathetic nervous system (SNS) and how the brain communicates with the body via the SNS.

The present technology is directed to methods for treating eating disorders, managing symptoms or sequelae associated with eating disorders, reducing a severity of eating disorders, and/or for reducing a risk associated with developing an eating disorder in patients via renal neuromodulation. In certain embodiments, the present technology is directed to beneficially improving one or more measurable physiological parameters associated with eating disorders in a patient via renal neuromodulation. Other embodiments of the present technology include performing therapeutically-effective renal neuromodulation on a patient to reduce a severity of neurobiological symptoms relating to an eating disorder. Further embodiments of the present technology include performing therapeutically-effective renal neuromodulation on a patient to reduce the risk of occurrence of an eating disorder in at-risk patients.

In yet another embodiment, a patient having had one or more previous episodes or diagnosis of an eating disorder can be treated with therapeutically-effective renal neuromodulation to reduce a risk associated with reoccurrence of the eating disorder or development of another eating disorder. In a particular embodiment, for example, the patient has experienced one or more periods of eating disorder indicators (e.g., excessive thinking about food, body or weight) that poses a measurable risk for experiencing a reoccurrence or a pattern of such symptoms, but the patient does not currently meet the standard for an eating disorder diagnosis. In another particular embodiment, the patient has had a previous, but not current, diagnosis of an eating disorder that poses a measurable risk for developing the same or a different related Axis I disorder (e.g., anxiety disorder, depression, etc.). In some embodiments, the patient exhibits one or more additional risk factors for the development of an eating disorder following a traumatic event, life change or stressful situation. Other embodiments of the present technology include performing therapeutically-effective renal neuromodulation on a patient prior to the patient experiencing a potentially life-debilitating or life-threatening episode. For example, the patient may be diagnosed with anorexia, depression, an anxiety disorder (e.g., general anxiety disorder, post-traumatic stress disorder (PTSD), etc.) and/or other psychotic disorder, have had one or more life threatening episodes due to lack of eating, or in another embodiment, the patient may also be experiencing physical health issues related to chronic/uncontrollable stress.

The present technology is further directed to methods for reducing an incidence of cardiovascular disease or a cardiovascular event in patients diagnosed with an eating disorder. In certain embodiments, for example, the present technology is directed to improving one or more measurable physiological parameters associated with cardiovascular health in the patient experiencing eating disorder symptoms or having an eating disorder diagnosis via renal neuromodulation. Other embodiments of the present technology include performing therapeutically-effective renal neuromodulation on a patient diagnosed with an eating disorder to reduce a severity of a cardiovascular condition. Further embodiments of the present technology include performing therapeutically-effective renal neuromodulation on a patient diagnosed with an eating disorder to reduce the risk of occurrence of a cardiovascular event in such patient in later life.

As discussed in greater detail below, therapeutically-effective renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-9. The embodiments can include, for example, modulating nerves proximate (e.g., at or near) a renal artery, a renal vein, and/or other suitable structures. Although many of the embodiments are described herein with respect to electrically-induced, thermally-induced, and chemically-induced approaches, other treatment modalities in addition to those described herein are within the scope of the present technology. Additionally, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-9.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. EATING DISORDERS

Eating disorders are categorized by abnormal obsession with food, control of food intake, body weight and/or shape, and other inappropriate relationships with food. As used herein "eating disorder" refers to any form of eating disorder or illness associated with abnormal eating habits or compulsive behaviors associated with overeating, undereating, or eating inappropriate or dangerous substances. As there are several forms of eating disorders that are distinguished by a spectrum of symptom types and severity as well as the persistence of the disorder in an affected individual, clinically-accepted diagnosis of an eating disorder, may be found in the American Psychiatric Association defines the criteria in its *Diagnostic and Statistical Manual of Mental Disorders* (DSM-5). While occasional abnormal eating episodes (i.e., overeating or lack of eating) are normal and/or can accompany periods of acute stress or result from a life event or circumstance, an eating disorder can be characterized by symptoms that are excessive, recurrent and/or non-temporary (e.g., longer than a month). In some situations, patients can be afflicted with more than one eating disorder. In all forms of eating disorders, however, affected and/or susceptible individuals may develop ongoing (chronic), short-term (acute) or recurring eating disorder episodes with potential for debilitating mental and physical health outcomes.

The most common form of eating disorder is binge-eating disorder, which is characterized by recurrent binge eating episodes during which a person feels a loss of control and marked distress over his or her eating. As a result, people with binge eating disorder can become overweight or obese. In diagnosing a binge-eating disorder, a clinician would assess (1) if the patient's eating takes place in a discrete period of time (e.g., within any 2-hour period), (2) if the patient is eating an amount of food that is definitely larger than what most people would eat in a similar period of time under similar circumstances, and (3) if the patient experiences a sense of lack of control over or while eating during the episode (e.g., a feeling that one cannot stop eating or control what or how much one is eating). Binge eating episodes would be additionally associated with three or more of the following indicators: eating much more rapidly than normal, eating until feeling uncomfortably full, eating large amounts of food when not feeling physically hungry, eating alone because of feeling embarrassed by how much one is eating, and feeling disgusted with oneself, depressed or very guilty afterward.

Bulimia Nervosa is also characterized by binge eating as discussed above, but further includes compulsory behavior that causes the individual to purge the food, such as, through self-induced vomiting, excessive use of laxatives or diuretics, by fasting, and/or through excessive exercise. People with bulimia can fall within the normal range for their weight, but they often fear gaining weight, want desperately to lose weight or are intensely unhappy with their body size and/or shape.

Anorexia Nervosa is characterized by significant and persistent reduction in food intake which leads to extremely low body weight in the context of age, sex and physical health. They present with a relentless pursuit of thinness and have a distorted view of their body image along with an intense fear of gaining weight. Despite that afflicted individuals are starved or severely malnourished, many people with anorexia see themselves as overweight.

Other feeding or eating disorders, as classified in the DSM-5, include pica and rumination disorders. Pica is the ingestion of non-nutritive substances (e.g., hair, chalk, paint chips, rocks, wood, metal, carpet, soap, etc.) deemed to be age inappropriate and occurring over at least a one-month period. Rumination is characterized by repeated, voluntary regurgitation (e.g., spewing up or spitting up of food) for a period of at least one month, and which is not attributable to vomiting or any related medical or gastrointestinal condition.

Persons with chronic (e.g., at least one month, greater than 2 months, greater than 3 months, greater than 6 months, between about 1 month and 1 year, or greater than 1 year, etc.), eating disorders (e.g., binge eating, bulimia, anorexia, pica, rumination, among others) report difficulties with work, school, home, relationships and/or social activities, and numerous studies have shown that this category of disorders causes clinically significant distress or impairment in social, occupational, or other important areas of functioning.

As discussed above, diagnosis of an eating disorder is based on the identification of the clinical criteria (e.g., symptoms and signs) as set forth in DSM-5. Clinicians and other mental health practitioners typically use conventionally accepted diagnostic test methods, such as screening tools (e.g., for use during diagnostic interviews, patient health questionnaires, etc.) for identifying eating disorder risk, severity and diagnosis. These screening tools are typically focused on core symptoms and indicators as set forth in DSM-5, but some screening tools provide further diagnostic capability to determine symptom severity, various specifiers, and/or other risk factors. For example, severity is typically determined by the degree of disability (e.g., cognitive, physical, social, occupational, etc.) or pain experienced by the patient as well as the duration of the symptoms. These screening tools are also designed to differentiate eating disorders from other mental disorders (e.g., anxiety disorders, depressive disorders, etc.). For example, patients can be diagnosed with an eating disorder and/or a measure of eating disorder severity can be determined using the Eating Disorder Examination Questionnaire (EDE-Q). Other questionnaires might be used to combine anxiety and depression measurements, such as the Hamilton Anxiety Rating Scale, the Hospital Anxiety and Depression Scale (HADS), and the Patient Health Questionnaire (PHQ-ADS). As disclosed herein, such screening tools can be used to provide a risk score for predicting a patient's eating disorder status with respect to disorder diagnosis, eating disorder severity and/or identifying at-risk populations.

Certain risk factors have been identified that may make an individual more likely (e.g., increase a risk) to develop an eating disorder during their lifetime. For example, some identified risk factors for increasing a likelihood of developing an eating disorder include having a family history and/or personal history of an eating disorder, depression, an anxiety disorder or other mental illness, experiencing adverse life events (e.g., illness, abuse, loss of a loved one, unemployment, psychological trauma, etc.), having experienced prior traumatic events, being a childhood survivor of abuse, experiencing trauma during childhood, experiencing parental loss or separation, having a history of substance abuse, experiencing a difficult relationship, being in a stressful situation, experiencing a major life change, experiencing an extended period of stress (e.g., chronic stress), physically inactive, and female gender, among others. Other factors include certain personality traits. For example, narcissistic personality disorder and borderline personality disorder are both predictive risk factors for eating disorders.

Patients presenting with an eating disorder may also experience other adverse mental and physical diseases and disorders. For example, eating disorders have high comorbidity with mental disorders such as major depressive disorder, anxiety disorder (e.g., general anxiety disorder, social anxiety disorder, panic disorder, obsessive compulsive disorder, etc.), substance and alcohol abuse, and attention-deficit hyperactivity disorder (ADHD). Further, cardiovascular disease, stroke, hypertension, obesity (e.g., high body mass index (BMI)), cancer, female infertility, and metabolic disorders, such as type 2 diabetes, among others are also highly comorbid with certain eating disorders. Without being bound by theory, it is possible that eating disorders share underlying neuroendocrine, metabolic and other psychophysiological patterns with these other disorders that either increase risk for the development of an eating disorder or reduce treatment success and/or increase risk for the development of these additional conditions.

A. Biophysical Characteristics of Individuals with Eating Disorders

Eating disorders belong to a mental disorder category encompassing complex and multifactorial disorders that are thought to be caused by many contributing factors. The underlying neurobiological and metabolic mechanisms or etiology of eating disorders are uncertain and/or may vary depending on the category of eating disorder; however, evidence suggests that psychological, genomic and other biological risk factors are present in patients identified with eating disorders. Moreover, neurobiological heterogeneity in monoaminergic transmitter systems, the hypothalamic-pituitary-adrenal (HPA) axis, metabolic hormonal pathways, inflammatory mechanisms, and psychophysiological reactive and neural circuits have been demonstrated between individuals diagnosed with eating disorders and healthy individuals (Lechin, F., et al., *Diabetes Metab Syndr Obes.*, 2010, 3: 311-317; Warren, M. P., *J Clin Endocrinol Metab*, 2011, 96: 333-343; Herpertz-Dahlmann, B., et al., *Eur Child Adolesc Psychiatry*, 2017, 26: 1031-1041; Mayhew, A. J., et al., *Neuroendocrinology*, 2018, 106: 292-306). In addition to differences between individuals diagnosed with an eating disorder and healthy individuals, those who do meet the criteria for a diagnosis of an eating disorder can vary in the severity of their symptoms as well as the type of symptoms they experience.

Psychological stress, including chronic stress, can have deleterious effects on the brain's neural circuits as well as whole-body physiological states, and is a crucial factor underlying mental disorders, with variation in stress susceptibility, responsivity and resilience providing variances in disorder presentation and severity (Halaris, A., *Curr Topics Behav Neurosci*, 2017, 31:45-70). The neuro-hormonal systems that play a critical role in stress responses and homeostasis include the HPA axis and noradrenergic systems. The noradrenergic system includes a dense network of axons that extend from the locus coeruleus in the brain stem throughout the brain including the hippocampus, amygdala, thalamus and hypothalamus, as well as projections that extend down the brain stem to synapse with sympathetic nerve fibers in the thoracic region.

Correlative links have been implicated between a variety of mood and cognitive disorders and chronic or prolonged hyperactivity of the sympathetic branch of the autonomic nervous system. As shown in FIG. 1, the SNS is a branch of the autonomic nervous system along with the enteric nervous system and parasympathetic nervous system. The SNS is primarily an involuntary bodily control system typically associated with stress responses. It is always active at a basal level (called sympathetic tone) and becomes more active during times of stress. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. The SNS regulates the function of virtually all human organ systems by localized release of catecholamines (e.g., norepinephrine) from sympathetic nerve terminals innervating these tissue and organ systems, spillover of norepinephrine from vascular neuromuscular junctions (the primary source of norepinephrine in plasma), and by systemic circulation of catecholamines (e.g., epinephrine, norepinephrine) released from the adrenal gland in response to acute, transient stress or threats. Long-term variations in basal levels, increases in basal levels due to aging, as well as spikes of circulating catecholamines from hyperactivity of the SNS responding to life circumstances can also exert more enduring regulatory effects on gene expression by altering constitutive gene expression profiles in a wide variety of tissues and organ systems.

In addition to release of norepinephrine from sympathetic nerve terminals innervating these tissue and organ systems, perivascular adipose tissue, which closely surrounds most blood vessels (except in the brain), has been shown to contain pools of norepinephrine. Renal perivascular adipose tissue, in particular, can release stored norepinephrine, thereby altering renal vascular function and contributing to spillover of norepinephrine to plasma.

Once released, norepinephrine binds adrenergic receptors on peripheral tissues. In addition, activation (e.g., norepinephrine release) of noradrenergic nuclei in the central nervous system (CNS) can result from transmitted impulses from activated afferent renal sympathetic neurons. Binding to adrenergic receptors either in the periphery or in the CNS causes a neuronal and hormonal response. The physiologic manifestations include pupil dilation, increased heart rate, occasional vomiting, and increased blood pressure. Increased sweating is also seen due to binding of cholinergic receptors of the sweat glands. It is known that long-term SNS hyperactivity has been identified as a major contributor to the complex pathophysiology of hypertension, states of volume overload (such as heart failure), and progressive renal disease, both experimentally and in humans. Moreover, correlative links between activation of the SNS and systemic inflammation, arterial stiffness, atherosclerosis, metabolic disorders, insulin resistance, and other cardiovascular conditions have been established. As mentioned above, many of these conditions are comorbid with eating disorders.

Increased levels of catecholamine (e.g., norepinephrine) spillover and secretion are associated with eating disorders. For example, higher levels of circulating catecholamines, such as norepinephrine (in the periphery and central nervous systems), have been reported in stress and fear-related disorders (e.g., anxiety disorders) as well as depression which share common underlying etiology with eating disorders. For example, activated noradrenergic system is implicated in psychological stress, which is one of the primary risk factors for eating disorder development. Without being bound by theory, this suggests that increased SNS activity is present in eating disorder patients.

Other indicators of increased SNS tone in patients with eating disorders include elevations in heart rate, blood pressure, skin conductance, and platelet activation as well as a decrease in heart rate variability (e.g., a measure of beat-to-beat fluctuations in heart rate). In contrast, healthy individuals that do not meet the criteria for an eating disorder may exhibit significantly lower plasma catecholamine levels and may not display other indicators of elevated SNS activity.

Without being bound by theory, increased levels of norepinephrine can account for many aspects of eating disorder-associated symptoms, including, for example, intense fear of gaining weight or becoming fat, cognitive behaviors that interfere with weight gain (e.g., calorie restriction, purging, use of laxatives, etc.), preoccupation or disturbance in the way one sees body weight or shape, eating large amount of food in a discrete amount of time (e.g., within a 2 hour period), sense of lack of control over eating, eating until uncomfortably full, eating large amounts of food when not feeling physically hungry, recurrent compensatory behavior to prevent weight gain (e.g., self-induced vomiting, misuse of laxatives, diuretics, or medications), fasting, excessive exercise, feeling ashamed or disgusted with oneself, or depressed, impaired concentration, irritability, and feelings of sadness or anxiousness. Hyperactive SNS activity in patients with eating disorders would also present an ongoing challenge to treatment success as levels of norepinephrine increase or spike in response to stressors and/or worsening psychological stress in these individuals.

Individuals with eating disorders also exhibit altered HPA axis function such as having elevated levels of corticotropin-releasing hormone (CRH) and increased nocturnal CRH activity, which initiates stimulation of the HPA axis in response to stress (e.g., psychological stress, etc.). Hyperactivity of the HPA axis as well as higher circulating cortisol (i.e., glucocorticoid) levels compared to healthy controls (e.g., patients without eating disorders) also exemplify HPA axis dysfunction in remitted as well as currently diagnosed patients. Decreased responsiveness to glucocorticoids (e.g., glucocorticoid resistance) and subsequent HPA axis dysfunction is a hallmark of major depression (Miller, A. H., et al., *Biol Psychiatry,* 2009, 65: 732-741), and may also be in related disorders (e.g., eating disorders, anxiety disorders). Alterations to HPA axis function, both reflecting a current mood state as well as long lasting changes to brain function, may be mediated, in part, by alterations in the glucocorticoid receptor. In particular, it has been demonstrated that patients with depression and anxiety disorders exhibit reduced glucocorticoid sensitivity, preferential expression of a dominate negative form (GR-$\beta$) of the glucocorticoid receptor, and increased levels of FKBP5, which is a co-chaperone of the glucocorticoid receptor that inhibits ligand binding and pathway activation (Menke, A., et al., *Genes, Brain and Behav,* 2013, 12: 289-296; Spijker, A. T. and van Rossum, E. F. C., *Neuroendocrinology,* 2012, 95:179-186; Miller, A. H., et al., *Biol Psychiatry,* 2009, 65: 732-741). Without being bound by a theory, an individual's level of chronic exposure to stress, and thereby cortisol exposure, in brain regions associated with emotion and cognition (e.g., the limbic system), may be important in the development or prediction of future risk of an eating disorder in the individual, and this additional major stress response system may determine longer-term patterns of stress responses in eating disorder patients.

CRH and norepinephrine are known to interact in regions of the brain involved in stress responses to increase fear conditioning, interfere in emotional response, cognition and encoding of emotional memories (Jedema, H. P. and Grace, A. A., *J Neurosci,* 2004, 24:9703-9713). Further reinforcing a prolonged psychological stress response and the pathophysiology of eating disorders, CRH is elevated in the locus coeruleus of eating disorder patients and has been shown to activate neurons in the locus coeruleus which would result in increased norepinephrine levels throughout the CNS.

Neuropeptide Y (NPY), a 36-amino-acid peptide transmitter that is expressed in brain regions that regulate stress and emotional behaviors, has shown to buffer stress responses and promote increased ability to cope with emotional trauma (Enman, N. M., et al., Neurobiol Stress, 2015, 1: 33-43; Sah, R. and Geracioti, T. D., *Mol Psychiatry*, 2013, 18:646-655). In particular, central nervous system NPY concentration levels may normally control or suppress pro-stress transmitters such as CRH and norepinephrine in the brain (Id.). However, both central and peripheral nervous system NPY concentrations are significantly lower in individuals with anxiety-related and mood disorders when compared to healthy controls (Id.), possibly attenuating the individuals' resilience and coping ability in response to psychological stress. Without being bound by theory, and since NPY functions to inhibit CRH and norepinephrine promotion of stress and fear responses, as well as reduces the release of norepinephrine from sympathetic neurons, decreased NPY activity may contribute to SNS hyperactivity in patients with eating disorders.

An additional physiological characteristic associated with an eating disorder includes a pro-inflammatory state, including chronic inflammation. For example, elevated levels of inflammatory cytokines, such as interleukin-6 (IL-6), IL-8, tumor necrosis factor-alpha (TNF-α) as well as other inflammatory markers, such as C-reactive protein (CRP), are elevated in individuals with mental disorders, and peripheral levels of these inflammatory markers correlate positively with eating disorder symptomology (e.g., anxiety, obsessive compulsive behavior, fatigue, cognitive dysfunction, impaired sleep). Moreover, higher levels of inflammatory biomarkers are associated with exacerbated eating disorder symptoms, and without being bound by theory, may pose an increased risk in the development of an eating disorder.

Mental disorders are also associated with increased activation of the transcriptional factor, nuclear factor-κB (NF-κB), which is activated by exposure to psychosocial stress and sympathetic nervous system outflow pathways, and is responsible for cytokine production. Cytokine-induced increases in neural activity in brain regions, such as the anterior cingulated cortex and the basal ganglia, have been associated the development of mood and anxiety symptoms, and are associated with alterations in brain neurotransmitter metabolism (e.g., serotonin, norepinephrine and dopamine), neuroendocrine function and neural plasticity (Id.). For example, cytokine-induced immune responses have shown to increase the number of reuptake pumps, thereby decreasing neurotransmitter availability, and shunting tryptophan away from the production of serotonin in the brain. Without being bound by theory, increased SNS activity coupled with reduced sensitivity to the anti-inflammatory effects of glucocorticoids (e.g., due to glucocorticoid resistance) as a result of chronic psychological stress, both contribute to chronic activation of inflammatory responses.

Currently prescribed treatment plans for patients diagnosed with eating disorders typically consist of psychotherapy, physical intervention and/or pharmaceutical drugs. Conventional drug therapies may be administered to address particular symptoms associated with eating disorders in attempts to lessen those particular symptoms. For example, anti-anxiety medication (e.g., benzodiazepines, buspirone, β-blocker, etc.), antidepressants (e.g., selective serotonin reuptake inhibitors (SSRIs) that raise the level of serotonin in the brain, tricyclic antidepressants, monoamine oxidase inhibitors (MAOIs), etc.), anti-psychotic drugs, anti-hypertensive drugs, mood stabilizers, etc., may provide mild to moderate and/or temporary relief from eating disorder symptoms, anxiety-related symptoms, cognitive and/or memory difficulties, etc. However, most patients do not get adequate treatment and for many patients, medications are ineffective. Moreover, drug adherence over several years or decades in a manner than maintains sleep quality, mood, anxiety disorder-related symptoms, blood pressure, etc., remains a challenge for most patients. For many patients, improvements may not be apparent until after up to 4 or more weeks of drug treatment, causing delays in ascertaining whether the prescribed drug or drug combination is suitable for the particular patient. Furthermore, some medications do not work or stop working effectively over time, and some become addictive and/or cause other intolerable side effects. Additional drawbacks to use of drugs for treating a patient with an eating disorder include the possibilities of adverse reactions associated with these medications (e.g., heart failure, hypotension, bradycardia, severe depressive episodes, suicide ideation, sexual dysfunction, weight gain or unhealthy weight loss, death, etc.), as well as other undesirable side-effects, on a patient-by-patient basis.

Additionally, pharmaceutical intervention for other contributors and risk factors associated with eating disorders further complicates drug administration and management of contraindications between anti-inflammatory medications, anti-hypertensive drugs, anti-anxiety drugs, antidepressant drugs, mood stabilizers among others administered to support patients with eating disorders, and adherence over years remains a challenge. Various psychotherapy treatments can be prescribed in combination with a medication plan or as a stand-alone treatment. While psychotherapy (e.g., cognitive-behavioral therapy, interpersonal therapy, etc.) may provide some patients with skills in new ways of thinking and behaving, it may not be effective for more severe forms of eating disorders such as anorexia, bulimia, and binge eating, among others. Some patients with severe or medication adverse and/or resistant disorders may be treated with several sessions of electroconvulsive therapy, phototherapy, deep brain stimulation and others with mixed results. Various aspects of the present technology address SNS effects on risk factors associated with eating disorders while overcoming these challenges.

B. Risk Factors Associated with Development of Eating Disorders and/or Related Conditions As discussed above, eating disorders are psychophysiological disorders encompassing dysregulation of complex neuro- and hormonal-biochemical pathways that are known to be caused by many contributing factors. While many biomarkers distinguishing patients with an eating disorder and healthy individuals demonstrate heterogeneity following pathogenesis in an individual, certain earlier-identifiable conditions as well as genetic and/or biophysical variances in a patient are recognized as being either contributory factors and/or predictors of a likelihood that a patient will develop an eating disorder or, in the case of remitted patients, a likelihood that the patient will redevelop the same eating disorder or develop a different eating disorder. In particular, many underlying conditions, genetic variances and other abnormalities detectable in individuals either prior to the development of an eating disorder or during remittance, may affect the likelihood of the individual subsequently developing one or more eating disorders. Such underlying conditions and genetic/biophysical variances constitute eating disorder predictors or risk factors.

As discussed above, some identified risk factors for increasing a likelihood of developing an eating disorder include certain demographic variables such as, for example, female gender, drug or alcohol abuse, and being physically inactive. Additionally, it has been shown that if the patient has a history of eating disorders, mental illness, has a family history of eating disorders, depression or other mental illness, has experienced one or more adverse life events (e.g., illness, abuse, loss of a loved one, unemployment, psychological trauma, etc.), has or is experiencing a difficult relationship, has experienced prior traumatic events, has had an adverse childhood experience, is currently in a stressful situation, has or is experiencing a major life change, or has or is experiencing an extended period of stress (e.g., chronic stress), among others, the patient has an increased likelihood of developing an eating disorder.

Without being bound by theory, increased SNS activity in the patient as a result of psychological and/or other forms of chronic stress can predispose the individual to developing an eating disorder. For example, chronic stress has been shown to alter neural circuits and structures in the brain (e.g., hippocampus, prefrontal cortex, etc.) (Pitman, R. K., et al., *Nat Rev Neurosci.*, 2012, 13: 769-787) that may increase the individual's sensitivity to contextual threat. Such sensitization of the SNS may be responsible for higher heart rates during a subsequent exposure to a trigger, stressful situation or a traumatic event, which may be a predictive risk for future development of a mood disorder accompanied by an eating disorder. Moreover, lower heart rate variability characterizes eating disorders and may also be predictive of eating disorder development. In certain embodiments, prior exposure to trauma (e.g., childhood abuse, prior sexual abuse, prior combat experience, etc.) may increase the individual's sensitization of the SNS, thereby lowering the threshold barriers for the development of an eating disorder.

While there is evidence for the presence of SNS hyperactivity in patients presenting with an eating disorder, there is further evidence that a strong adrenergic response to a traumatic event or other adverse life circumstance may mediate or in part contribute to the development of an eating disorder in certain individuals. Some biochemical inducements of the increase in norepinephrine release in response to SNS activation include genetic and/or other inhibition paths that lower NPY levels, as well as lower numbers or affinity of α2-adrenergic receptors (Pitman, R. K., et al., *Nat Rev Neurosci.*, 2012, 13: 769-787; Sherin, J. E., et al., *Dialogues Clin Neurosci*, 2011, 13: 263-278). Additionally, there is evidence that a pro-inflammatory state (e.g., as indicated by increased levels of inflammatory cytokines) may increase risk or vulnerability for development of an eating disorder particularly when patients present with chronic stress. For example, it has been shown that increased levels of CRP (e.g., greater than about 3 mg/L; greater than about 5 mg/L; etc.) were predictive of psychological distress and depression, and without being bound by theory, elevated levels of CRP can present as an additional risk factor that can establish a predictive risk for the development of an eating disorder.

Correlative links between activation of the SNS and high blood pressure, coronary heart disease, stroke, systemic inflammation, arterial stiffness, endothelium dysfunction, atherosclerosis, metabolic disorders, insulin resistance, end organ damage, obesity (e.g., high body mass index (BMI)), and other cardiovascular conditions have also been established. As discussed above, these conditions/diseases have further been shown to be correlative with an incidence of anxiety-related disorders and various eating disorders. As such, it is posited that these conditions/diseases, which are indicative of chronic activation of SNS, present as risk factors that can establish a predictive risk for the development of an eating disorder. In fact, anxiety disorders and other mood disorders are more prevalent in people who have suffered a major cardiac event. Strokes (e.g., acute ischemic stroke, lacunar stroke, transient ischemic attack (TIA), hemorrhagic stroke, etc.) are also highly associated with the development of mental disorders (e.g., anxiety, depression), and post-stroke mental disorders are associated with increased morbidity and mortality in such patients.

Additionally, with respect to blood pressure regulation, the nocturnal blood pressure of healthy individuals drops or "dips" more than 10% of the average daytime blood pressure value, which is followed by an increase in blood pressure with arousal from sleep, known as the morning surge in blood pressure (MSBP). In contrast, "elevated," i.e. limited drops in blood pressure during the nighttime (e.g., nighttime blood pressure reduction that is less than 10% of average daytime blood pressure) as well as excessive surge in MSBP (e.g., early morning hours), is associated with an increased risk of cardiovascular events and strokes even in normotensive patients (FitzGerald, L., et al., *J Hum Hypertens*, 2012, 26: 228-235; Kario, K. and Hamasaki, H., *J Clin Hypertens*, 2015, 17: 682-685). Several mental and mood disorders correlate with higher MSBP and the increase in MSBP is proportional to the severity of the disorder-related symptoms and is irrespective of "dipping" status (Id.). Men and older populations of patients further demonstrate "non-dipping" nocturnal blood pressure which is further associated with more sleep-related symptoms and poorer overall sleep quality as well as increased risk in cardiovascular events (Id.). Psychological risk factors, such as depression and anxiety, are reported to influence cardiovascular events and to impact hypertension, and excessive MSBP and/or "non-dipping" nocturnal blood pressure may be risk factors for the development and/or the severity for hypertension, cardiovascular disease and stroke. Moreover, excessive MSBP and/or "non-dipping" nocturnal blood pressure may be risk factors for the development or progression of eating disorders in such patients.

In addition to chronic and/or acute SNS hyperactivity, increased glucocorticoid (e.g., cortisol) levels, and HPA axis dysfunction, e.g., as a measurement of basal cortisol levels in response to awakening as an indicator for endogenous stress response, provide additional risk factors that can be considered in establishing a predictive risk assessment for the development of an eating disorder in a patient. For example, and without being bound by theory, an abnormally high measurement of cortisol awakening rise (CAR), which reflects the natural response to awakening with a normal/natural increase in cortisol levels, may not only be characteristic of patients with an mental and mood disorders, but can be predictive for developing an eating disorder, and thereby provides an additional risk factor of subsequent eating disorder development. Without being bound by theory, it is thought that high levels of cortisol resulting in glucocorticoid resistance and increased HPA axis activity fails to inhibit CRH/norepinephrine responses to stress and further exacerbates cognitive dysfunction (e.g., memory deficits, inability to concentrate) and eating disorder-related symptoms in these individuals.

In addition to predisposition factors associated with activation of the SNS and other demographic risk factors, certain genetic variations among individuals have also been shown to be predictive risk factors for the development of mental and mood disorders. Some of these genetic risk factors are common to both major depressive disorder, anxiety disorder and eating disorders. For example, genes that affect risk for development of an eating disorder may also influence risk for other psychiatric disorders and vice versa. As with other mental disorders, influences on eating-related disorders are likely polygenic; at least 17 single nucleotide polymorphisms (SNPs) in 15 different genomic regions have been associated with depression and related psychiatric disorders in at least one published study (Hyde, C. L., et al., *Nature Genet,* 2016, 48: 1031-1036). These and other genetic variants demonstrated to influence risk for anxiety, depression, and associated eating disturbance symptoms include genes involved in HPA axis regulation, the locus coeruleus/noradrenergic system, dopaminergic and serotonergic systems (e.g., regulation of synapses, monoamine metabolism, etc.) and other neurodevelopment programs (Hyde, C. L., et al., *Nature Genet,* 2016, 48: 1031-1036; Converge Consortium, *Nature,* 2015, 523: 588-591; Miller, A. H., et al., *Biol Psychiatry,* 2009, 65: 732-741).

With respect to HPA axis regulation, several known genetic variations in the glucocorticoid receptor gene, NR3C1, affect glucocorticoid sensitivity (Spijker, A. T. and van Rossum, E. F. C., *Neuroendocrinology,* 2012, 95:179-186). For example, the ER22/23EK polymorphism, which is associated with mild glucocorticoid resistance, and the BclI polymorphism, which is associated with increased stability of the mRNA of the dominant negative GR-β isoform, are both associated with a higher risk of developing a mood and related disorders (Id.). Additionally, carriers of particular heritable polymorphisms in the genes encoding for FK506-binding protein 5 (FKBP5; co-chaperone of the glucocorticoid receptor that inhibits ligand binding and pathway activation) leading to increased intracellular FKBP5 protein expression, the CRH receptor 1 (CRHR1 rs242939 polymorphism), and serotonin transporter (SLC6A4; responsible for serotonin transport and reuptake) have been shown to be overrepresented in patients with depression, and carriers of these genetic variants may have an increased likelihood of developing some types of eating disorders (Mahan, A. L. and Ressler, K. J., *Trends Neurosci,* 2012, 35: 24-35; Pitman, R. K., et al., *Nat Rev Neurosci.,* 2012, 13: 769-787; Spijker, A. T. and van Rossum, E. F. C., *Neuroendocrinology,* 2012, 95:179-186; Miller, A. H., et al., *Biol Psychiatry,* 2009, 65: 732-741).

Further evidence has suggested that in addition to genotype, epigenetic factors such as gene methylation, histone deacetylation, and other gene expression differences can influence or accompany the development of eating and other mental disorders, and these genetic profiles can be screened to determine patients presenting certain genetic pre-dispositions associated with high or increased risk of developing an eating disorder (Spijker, A. T. and van Rossum, E. F. C., *Neuroendocrinology,* 2012, 95: 179-186; Mahan, A. L. and Ressler, K. J., *Trends Neurosci,* 2012, 35: 24-35; Pitman, R. K., et al., *Nat Rev Neurosci.,* 2012, 13: 769-787).

Once a clinical eating disorder is present, a host of physiological changes occur in the patient, including SNS and immune system activation/hyperactivation, neuroendocrine changes, rhythm disturbances, oxidative stress, platelet hypercoagulability and endothelial dysfunction, all of which exert a negative impact on cardiovascular health. As discussed above, eating and other mental disorders are characterized by, among other things, elevated SNS activity, reduced heart rate variability, increased plasma cortisol levels and elevated inflammatory responses, all of which are associated with increased risk of cardiovascular disease (Brown, A. D., et al., *CNS Drugs,* 2009, 23:583-602). In particular, psychological stress accompanying an eating disorder causes dysregulation of the SNS and the HPA axis which can precipitate numerous downstream physiological effects throughout the body, including hypertension, left ventricular hypertrophy, coronary vasoconstriction, endothelial dysfunction, platelet activation and the production of pro-inflammatory cytokines, all of which carry an elevated risk of ventricular arrhythmias and myocardial infarction (MI). Additionally, eating disorders have been shown to be associated with increased morbidity and mortality in patients having cardiovascular disease and/or precipitate heart failure (e.g., anorexia). Without being bound by theory, mental stress (which accompanies and/or at least partially precipitates eating disorders) has been shown to activate cardiac sympathetic nerves with downstream effects of heart rhythm disturbances, increased risk of ventricular arrhythmias, decreased blood flow, left ventricular hypertrophy, MI and sudden death. Furthermore, essential hypertension can be triggered by and maintained by chronic psychological stress. Accordingly, eating disorders are a risk factor for the development of cardiovascular disease and stroke, with the relative risk level proportional to the severity of disorder in the patient. Furthermore, eating disorders in patients may increase future risk of stroke and transient ischemic attacks (TIAs). Excess stroke and TIA risk associated with eating disorders may stem from activation of the HPA axis, elevated catecholamines, and elevated inflammatory responses (e.g., increased CRP, IL-6, etc.) which are all related to stroke risk.

C. Identification of Patients or Cohorts Diagnosed with an Eating Disorder or at Risk of Developing an Eating Disorder Patients presenting with a high likelihood of having an eating disorder can include patients presenting with one or more of (1) eating disorder symptoms (e.g., intense fear of gaining weight or becoming fat, behaviors that interfere with weight gain (e.g., calorie restriction, purging, use of laxatives, etc.), disturbance in the way one sees body weight or shape, eating large amount of food in a discrete amount of time (e.g., within a 2 hour period), sense of lack of control over eating, eating until uncomfortably full, eating large amounts of food when not feeling physically hungry, recurrent compensatory behavior to prevent weight gain (e.g., self-induced vomiting, misuse of laxatives, diuretics, or medications), fasting, excessive exercise, feeling ashamed or disgusted with oneself, or depressed, etc.), (2) family history of depression, anxiety disorder or other mental illness, (3) prior diagnosis of an acute or chronic stress disorder, (4) prior diagnosis of any mood disorder (e.g., depression, anxiety, bipolar, sleep disorder, etc.), and/or (5) depression symptoms (e.g., depressed mood for most of the day, anhedonia, psychomotor agitation or retardation nearly every day, anergia, poor appetite or overeating, low self-esteem or feelings of worthlessness, changes in cognitive ability, and/or negative feelings about self or the world). Patients demonstrating certain risk factors or eating disorder symptoms may also have an increased likelihood of having an eating disorder if they exhibit with one or more of elevated SNS activity (e.g., catecholamines detected in urine or plasma), low central nervous system NPY levels, elevated cortisol levels, glucocorticoid resistance (e.g., as assessed via dexamethasone suppression test), elevated CAR, low heart rate variability, elevated MSBP, limited or no "dipping" of nocturnal blood pressure, elevated levels of serum inflammatory cytokine levels (e.g., IL-6, IL-8, TNF-α, CRP, etc.), and/or endothelial dysfunction.

Some patients may also present with comorbid conditions or diseases such as cardiovascular disease, having suffered a major cardiac event (e.g., MI, coronary artery bypass surgery), having had a stroke or risk of stroke, hypertension or pre-hypertension, ventricular arrhythmias, left ventricular hypertrophy, above-normal cholesterol levels, atherosclerosis, insulin resistance or other metabolic disorder, arterial stiffening or aneurysm(s), obesity or being overweight (e.g., high BMI), cancer, and/or patients with active substance abuse, a history of substance abuse, or prior mental disorder.

In certain embodiments, the patient can present with one or more risk factors and/or comorbid conditions associated with an increased likelihood of having an eating disorder. However, in other embodiments, such associated conditions may not be present in a patient having an eating disorder and/or at risk of developing an eating disorder. For example, the patient may be normotensive, have no evidence of cardiovascular disease, normal BMI, normal insulin sensitivity, and/or no elevated levels of inflammatory biomarkers.

Patients presenting with a high or increased risk of developing an eating disorder can include patients having one or more demographic or biophysical risk factors as described herein and who have not met the diagnosis standard as set forth in DSM-5 and/or patients in which one or more eating disorder screening tools or instruments used to give a professionally-accepted diagnosis have not confirmed an eating disorder. However, such patients may present one or more risk factors associated with an increased likelihood of developing an eating disorder. For example, the patient may have an increased likelihood of a present condition progressing toward an eating disorder, such as a patient presenting some but not a qualifying number of symptoms on the DSM-5, or in another embodiment, a patient may present a qualifying number of symptoms but has not experienced a threshold level of severity for one or more of those symptoms. In another example, the patient may demonstrate a combination of described risk factors (e.g., elevated SNS tone, high CAR, glucocorticoid resistance, elevated levels of CRP, low levels of central NPY, having experienced depressive episodes and/or anxiety attacks, history of child abuse or trauma, and/or family history of anxiety disorder, depression and/or other mental illness, etc.) and currently be experiencing chronic and/or excessive psychological stress (e.g., experiencing major life change, a difficult relationship, illness or disease of self or loved one, death of loved one, occupational stress, etc.).

In particular embodiments, patients having an increased risk of developing a moderate or severe eating disorder may have, for example, mild or acute eating disorder symptoms and demonstrate one or more of the following risk factors: (1) previously experienced traumatic events or experiences, (2) personal history of an eating disorder, (3) family history of depression, anxiety disorder or other mental illness, (4) prior diagnosis of acute stress disorder, (5) prior diagnosis of any mood disorder (e.g., depression, anxiety, bipolar, panic disorder, etc.), and/or (6) depression symptoms (e.g., depressed mood for most of the day, anhedonia, psychomotor agitation or retardation nearly every day, anergia, poor appetite or overeating, low self-esteem or feelings of worthlessness, changes in cognitive ability, and/or negative feelings about self or the world). Further risk factors for the development of an eating disorder in patients can include physiological markers such as elevated SNS activity (e.g., increased levels of catecholamines as detected in urine or plasma), elevated cortisol levels, low central nervous system NPY levels, glucocorticoid resistance (e.g., as assessed via dexamethasone suppression test), elevated CAR, low heart rate variability, elevated MSBP, limited or no "dipping" of nocturnal blood pressure, low baroreceptor sensitivity (e.g., an assessment of cardiovascular autonomic neuropathy), and/or elevated levels of serum inflammatory cytokine levels. A patient at-risk of developing an eating disorder may be hypertensive or pre-hypertensive and/or show elevated SNS tone in the form of blood pressure dysregulation (e.g., elevated 24-hour blood pressure variability). However, in many instances, patients having an eating disorder or being at-risk of developing an eating disorder can have normal blood pressure levels (e.g., do not have hypertension or pre-hypertension).

In some embodiments of the present technology, the patient can have a calculated risk score for (i) determining an eating disorder status (e.g., diagnosis, severity, etc.) or (ii) the prediction of developing an eating disorder that is above a threshold eating disorder risk score. Such a calculated eating disorder risk score can indicate a likelihood of an eating disorder diagnosis or, in another embodiment, a likelihood of developing an eating disorder. In one embodiment, for example, a calculated eating disorder risk score for determining an eating disorder status can be based upon one or more data sets known in the art. For example, an eating disorder risk score based upon the Eating Disorder Examination Questionnaire (EDE-Q). The EDE-Q, among other assessment tools, can be used to establish an eating disorder risk score for determining an eating disorder status (e.g., diagnosis/severity), and can be based upon an analysis of the patient's assessment across multiple possible risk factors. For example, the patient can be queried and assessed for core eating disorder symptoms indicated in the DSM-5 and the International Statistical Classification of Diseases and Related Health Problems (ICD-10) classification systems to determine if a patient has a mild, moderate, or severe eating disorder. One of ordinary skill in the art will recognize that the EDE-Q scale study is only one study in which a risk score calculation can be developed and applied. Other published data sources documenting multiple possible risk factors and corresponding scores may use any of many well described techniques. Such techniques for developing tools to calculate an eating disorder risk score could be empirical, based on multivariate regression, or using artificial intelligence (e.g. Bayesian probability, machine learning, etc.) among other techniques known in the art.

In other embodiments, a patient presenting a high or increased risk of developing an eating disorder can have a genetic disorder or determined genetic pre-disposition to developing an eating or other associated mental disorder. For example, specific forms (e.g., polymorphisms) of the glucocorticoid receptor gene, NR3C1, affect glucocorticoid sensitivity and additional polymorphisms in the gene known as FKBP5, a co-chaperone of the glucocorticoid receptor, is associated with increased glucocorticoid resistance and increased risk for anxiety-related disorders. Additionally, carriers of polymorphisms in the genes encoding for the CRH receptor 1 are associated with an increased likelihood of developing a mood disorder. As evidence has suggested that genotype, gene methylation, histone deacetylation, and gene expression differences among other epigenetic factors, influence or accompany the development of eating disorders, these genetic profiles can be screened to determine patients presenting certain genetic pre-dispositions associated with high or increased risk of developing an eating disorder.

A patient suspected of having an eating disorder can be evaluated for a level of dysfunction or severity of symptoms and/or sequelae associated with eating disorders. Evaluation of core symptoms (e.g., intense fear of gaining weight or becoming fat, behaviors that interfere with weight gain (e.g., calorie restriction, purging, use of laxatives, etc.), disturbance in the way one sees body weight or shape, eating large amount of food in a discrete amount of time (e.g., within a 2 hour period), sense of lack of control over eating, eating until uncomfortably full, eating large amounts of food when not feeling physically hungry, recurrent compensatory behavior to prevent weight gain (e.g., self-induced vomiting, misuse of laxatives, diuretics, or medications), fasting, excessive exercise, feeling ashamed or disgusted with oneself, or depressed, etc.), can include a self-reporting or assessment of changes from a person's usual level of function (e.g., prior to on-set of symptoms) to a current condition. Evaluation input may also come from trusted sources (e.g., trusted family members, friends, primary physician, etc.) that can provide information on changes in performance on daily activities, job/employment performance, behavior or mood changes, sleep patterns, as well as angry outbursts, irritability or aggression and/or other risky or destructive behaviors, etc.

Physicians or other qualified clinicians may also administer one or more questionnaires or diagnostic tests, such as screening tools, to assess eating disorder risk, severity and diagnosis. Eating disorder screening tools such as the EDE-Q, as well as other screening instruments that look at multiple risk factors for predicting the patient-specific clinical features along with eating disorder status can be utilized in the assessment process. One of ordinary skill in the art will recognize other eating disorder tests and scales that can be used to determine the status of an eating di of a patient. In some embodiments, for example, a patient may be suspected of having an eating disorder based upon a single test score or outcome, combined test scores from multiple tests, or one or more test scores from multiple tests. Diagnosis can be made based upon, for example, meeting or exceeding a threshold test score. In other embodiments, a patient may demonstrate an increase in symptom severity as reflected in test scores taken over time. For example, a particular patient may show an increase in eating disorder risk via a result in a test score between taking tests two weeks after on-set of symptoms, one month after on-set of symptoms, six months after on-set of symptoms, and a year or more after on-set of symptoms. Cognitive functioning (e.g., cerebral activities encompassing reasoning, memory, attention, and language), emotional/social functioning (e.g., traits and abilities involving positive and negative aspects of social and emotional life like empathy, interpreting emotion, speed and intensity of emotion generation, and efficacy of coping with negative emotions, etc.), and sleep dysfunction-associated symptoms, as well as other data that can be collected in an evaluation of a patient, are based on self-report, observational (behavioral), or psychological data.

In a particular example, if a patient could respond (or a clinician could so indicate with respect to a patient) in affirmation (i.e., answering "yes") and/or if the a patient can indicate at least a moderate level of severity to one or more of the following statements, then the patient could be diagnosed with an eating disorder and, in some embodiments, be treated with renal neuromodulation to treat the eating disorder: Over the past month, and at a frequency of less than once a week, once or twice a week, or three or more times a week—
  a) you deliberately try limiting the amount of food you eat,
  b) you have gone for long periods of time without eating anything,
  c) you have tried to exclude from your diet foods that you like,
  d) you have a definite desire to have an empty stomach,
  e) you have a definite desire to have a totally flat stomach,
  f) thinking about food, eating or calories makes it difficult concentrate,
  g) thinking about shape or weight of your body makes it difficult to concentrate,
  h) you have a definite fear of losing control over eating,
  i) you have a definite fear that you might gain weight,
  j) you have felt fat, and
  k) you have a strong desire to lose weight, Additional screening tools or eating disorder risk score calculating tools may ask additional questions to identify the presence or absence of known eating disorder risk factors. For example, a patient may be asked to respond to one or more of the following questions in an assessment:
  Do you have any medical conditions?
  Have you lost interest in hobbies or activities?
  Do you feel sad, irritable, or hopeless?
  Do you feel nervous or worried?
  Do you think something is wrong with your body?
  Do you have a personal or family history of an eating disorder or mental illness?
  How many adverse life events (e.g., major illness, abuse, loss of a loved one, unemployment, psychological trauma, etc.) have you experienced that has caused you either high levels of stress or chronic (e.g., greater than one year) stress?
  Did you experience traumatic life events and/or abuse as a child or adolescent?

Physicians or other qualified clinicians may also administer one or more questionnaires or diagnostic tests, such as screening tools, to assess depression symptoms that may accompany core eating disorder symptoms. For example, the Patient Health Questionnaire (PHQ-2) scale is a two-item depression screener as exemplified in the following questions:
  1. Have you ever had a period of two weeks or longer when you were feeling depressed or down most of the day or nearly every day?
  2. Have you ever had a period of two weeks or longer when you were uninterested in most things or unable to enjoy things you used to do?

A patient having eating disorder symptoms and one or more depression symptoms can be a candidate for renal neuromodulation.

In addition to self-reporting, observational, or other psychological data, a patient may also be evaluated for physiological data. Accordingly, a patient may demonstrate one or more physiological parameters associated with an eating disorder or, in other embodiments, with chronic psychological stress. Non-limiting examples of eating-associated physiological parameters may include low heart rate variability (e.g., as assessed by Standard Deviation NN intervals (SDNN)), decreased baroreceptor sensitivity (as an assessment of cardiovascular autonomic neuropathy), heightened heart rate responses to stimuli/stress (e.g., via Stroop Color Test or Cold Pressor Test), elevated muscle sympathetic nerve activity (MSNA; a marker of SNS activity), elevated systolic blood pressure, increased MSBP, lack of or low levels of nocturnal blood pressure "dipping", higher skin conductance (e.g., a measure of sweat activity thought to be under SNS influence), higher resting heart rate, disrupted sleep patterns or low quality sleep, elevated peripheral inflammatory markers (e.g., IL-6, IL-8, CRP, TNF-$\alpha$, etc.), low NPY levels (e.g., in the CNS and plasma), and other measures of sympathetic activity (e.g., increased renal and/or total body norepinephrine spillover, increased plasma norepinephrine levels, increased urine levels of norepinephrine and metabolites thereof, etc.). Further physiological parameters that can be risk factors for an eating disorder may include increased cortisol levels, glucocorticoid resistance (e.g., as assessed via dexamethasone suppression test), previous traumatic brain injury (TBI), and/or decreased levels of neurotransmitter receptors (e.g., GABA, 5-HT/serotonin, dopamine) in the brain (e.g., as assessed via administered radioligands followed by positron emission tomography (PET)).

In accordance with aspects of the present technology, patients presenting with one or more risk factors for having an eating disorder, having a calculated eating disorder risk score, and/or one or more risk factors for developing an eating disorder can be candidates for treatment for an eating disorder. In other embodiments, some patients may also be candidates for renal neuromodulation for the prevention of developing an eating disorder in the patient. As noted above, renal neuromodulation is expected to efficaciously treat an eating disorder including one or more symptoms associated with an eating disorder. Renal neuromodulation is also expected to efficaciously prevent an incidence of, reduce a severity of, or slow a progression of an eating disorder. Renal neuromodulation is further expected to improve a patient's calculated eating disorder risk score correlating to an eating disorder status/diagnosis.

In certain embodiments, for example, renal neuromodulation treats several clinical conditions characterized by increased overall sympathetic activity and, in particular, conditions associated with central sympathetic overstimulation such as pre-hypertension, hypertension, blood pressure variability, heart rate variability, vascular disease (e.g., vessel stiffening), metabolic syndrome, insulin resistance, diabetes, cancer, cognitive impairment (e.g., which can progress to dementia), systemic inflammation, depression, and anxiety disorder, among others, that may be associated with and/or contribute to a severity or progression of an eating disorder in a patient. The reduction of afferent neural signals typically contribute to the systemic reduction of sympathetic tone/drive, and renal neuromodulation is expected to be useful in treating several conditions associated with systemic sympathetic overactivity or hyperactivity. For example, and in accordance with other aspects of the present technology, patients presenting with one or more risk factors for having an eating disorder and/or having a positive clinical diagnosis for an eating disorder can be candidates for renal neuromodulation treatment for preventing, reducing an incidence of, and/or reducing a severity of a cardiovascular condition (e.g., coronary heart disease, MI, left ventricular hypertrophy, ventricular arrhythmias, etc.) and/or stroke (e.g., acute ischemic stroke, lacunar stroke, transient ischemic attack (TIA), hemorrhagic stroke, etc.) in the patient. In other embodiments, treating patients having an eating disorder in younger (e.g., 18-40 years of age) or in middle-aged (e.g., 40-65 years of age) patients may reduce an incidence of or improve an outcome of many comorbid conditions and diseases including, but not limited to, cardiovascular disease, stroke, metabolic disorders, diabetes, elevated cholesterol, obesity, cancer, dementia, etc. Accordingly, in particular examples, patients having or at risk of having an eating disorder and who are suitable candidates for treatment via renal neuromodulation can be between the ages of 18 and 45, between the ages of 18 and 30, between the ages of 20 and 40, or between the ages of 20 and 35. In other embodiments, the patients may be between the ages of 35 and 65, between the ages of 45 and 65, between the ages of 50 and 70, or the patient can be at least 35 years old, or at least 18 years old.

II. RENAL NEUROMODULATION FOR TREATING EATING DISORDERS AND/OR REDUCING A RISK ASSOCIATED WITH THE DEVELOPMENT OF AN EATING DISORDER

Therapeutically-effective renal neuromodulation can be used for the treatment of an eating disorder or for the treatment of one or more symptoms and/or sequelae associated with an eating disorder, the management of an eating disorder, or to reduce an incidence of an eating disorder in patients identified as having a risk of developing an eating disorder at a future time. In further embodiments, therapeutically-effective renal neuromodulation can be used for treating a patient (e.g., a patient having one or more risk factors associated with developing an eating disorder) prior to the development of one or more comorbid conditions (e.g., substance and alcohol abuse/addiction, depression and/or depressive disorder, psychotic and/or personality disorders, cardiovascular disease, stroke, hypertension, obesity (e.g., high BMI), metabolic disorders, such as type 2 diabetes, cancer, and cognitive impairment (e.g., leading to dementia), etc.) and for reducing a risk associated with developing an eating disorder.

In other embodiments, therapeutically-effective renal neuromodulation can be used to treat eating disorder patients or patients diagnosed with an eating disorder to reduce an incidence of cardiovascular disease (e.g., coronary heart disease, etc.) or a cardiovascular event (e.g., MI, stroke, etc.) in the patient. In further embodiments, therapeutically-effective renal neuromodulation can be used for treating a patient having an eating disorder to improve one or more parameters associated with cardiovascular health, or to reduce a severity of a cardiovascular condition.

While sympathetic drive regulation can have adaptive utility in maintaining homeostasis or in preparing many organs in the body for a rapid response to environmental factors, chronic activation of the SNS (e.g., associated with acute stress syndrome, chronic stress, primary aging, age-associated obesity, etc.) is a common maladaptive response that can contribute to diseases/conditions (e.g., hypertension, systemic or localized inflammation, vascular remodeling, atherosclerosis, obesity, insulin resistance, metabolic syndrome, etc.) or predispose individuals to psychophysiological adaptations that can increase a patient's risk of developing an eating disorder and/or drive progression and/or severity of an eating disorder in a patient. Excessive activation of the renal sympathetic nerves in particular has been identified experimentally and in humans as a likely contributor to the complex pathophysiology of hypertension, states of volume overload (such as heart failure), systemic inflammation, and progressive renal disease. As examples, radiotracer dilution has demonstrated increased renal norepinephrine spillover rates in patients with essential hypertension.

Aspects of the present technology include targeting renal nerve fibers for neuromodulation in patients (1) having been diagnosed with an eating disorder, (2) demonstrating one more physiological and/or psychological symptoms associated with an eating disorder, and/or (3) having an increased risk associated with developing an eating disorder. Targeting renal nerve fibers for neuromodulation in patients can effectively attenuate neural traffic along the sympathetic nerves. Without being bound by theory, attenuation of neural traffic along renal sympathetic nerves can be used, for example, to treat or prohibit one or more hallmark symptoms associated with an eating disorder, decrease systemic inflammatory responses associated with an eating disorder, and/or decrease a level of severity of an eating disorder and/or reduce a number of symptoms associated with an eating disorder in the patient. In yet another embodiment, attenuation of neural traffic along renal sympathetic nerves in an individual having one or more risk factors associated with developing an eating disorder can be used for reducing a risk associated with developing an eating disorder.

As discussed above, several diseases and conditions have high comorbidity with an eating disorder diagnosis, including, for example, substance and alcohol abuse/addiction, depression and/or depressive disorder, anxiety disorder (e.g., general anxiety disorder, social anxiety disorder), PTSD, psychotic and/or personality disorders, cardiovascular disease, stroke, hypertension, obesity (e.g., high BMI), metabolic disorders, such as type 2 diabetes, cancer, chronic kidney disease, peripheral artery disease, and cognitive impairment (e.g., leading to dementia). In certain embodiments, patients having an eating disorder and one or more comorbid conditions and/or diseases can be treated with renal neuromodulation to treat and/or reduce severity of the eating disorder and/or the one or more comorbid conditions/diseases. In another example, renal neuromodulation can be used to therapeutically treat a patient diagnosed with an eating disorder for preventing and/or reducing an incidence of developing one or more comorbid conditions/diseases, including those conditions/diseases wherein chronic SNS activity is known to be a contributing factor (e.g., hypertension, cardiovascular disease, etc.).

In one example, renal neuromodulation can be used to reduce a patient's systolic blood pressure, including a MSBP and/or a nocturnal blood pressure level. In another example, renal neuromodulation can be used to increase heart rate variability (e.g., the beat-to-beat fluctuations in heart rate) in a patient. In other embodiments, attenuation of neural traffic along renal sympathetic nerves can be used to treat or prevent metabolic disorders, obesity and/or insulin resistance in the patient having an eating disorder or at increased risk associated with developing an eating disorder. In yet a further embodiment, renal neuromodulation can be used to lower one or more levels of inflammatory biomarkers in a patient.

Certain effects of chronic SNS activation (such as resulting from chronic psychological stress) that take place prior to experiencing eating disorder symptoms may be associated with an increased risk of developing an eating disorder. Many of these effects may not yield noticeable signs or symptoms associated with a disease; however, the effects of chronic SNS activation can cause unseen damage to cardiac tissue, brain tissue, and/or vascular tissue, as well as disrupt normal neurophysiological and hormonal balances throughout the body prior to the appearance of quantifiable disease indicators typically associated with maladaptive SNS activation and/or prior to exposure to experiencing eating disorder symptoms in the predisposed or at-risk individual. Accordingly, in one embodiment, neuromodulation treatment can be used to treat patients having a high risk of developing an eating disorder. For example, patients may present one or more risk factors for developing an eating disorder (e.g., having been diagnosed with chronic stress, having an elevated heart rate, having reduced heart rate variability, having elevated cortisol levels and/or CRH levels, presenting with glucocorticoid resistance, elevated CAR, low levels of central NPY, having elevated systemic plasma levels of inflammatory biomarkers (e.g., IL-6, IL-8, TNF-α, CRP, etc.), having high blood pressure, having a genetic predisposition (e.g., polymorphisms in genes encoding for NR3C1, FKBP5, CRHR1, TNF-α, etc.). In other examples, such patients having a high risk of developing an eating disorder may present one or more social or demographic risk factors for the development of an eating disorder (e.g., adverse childhood experience(s), personal or family history of having an eating disorder, depression or mental illness, anxiety disorder, experiencing adverse life events, prior exposure to trauma, history of substance or alcohol abuse, being in a stressful situation or relationship, physically inactive, female gender, etc.).

In still further embodiments, neuromodulation treatment can be used to treat patients for improving an eating disorder risk score for a patient diagnosed with an eating disorder. Such a risk score may be determined, for example, using an eating disorder screening tool for determining a severity of an eating disorder in the patient. For example, certain patients can have an eating disorder risk score above a threshold eating disorder risk score, can have one or more eating disorder risk factors, have a combination of eating disorder risk factors, etc., and renal neuromodulation can be used to therapeutically reduce (a) systemic plasma levels of norepinephrine from, e.g., spillover from innervation of smooth muscle surrounding blood vessels, (b) systemic plasma levels of inflammatory biomarkers (e.g., IL-6, IL-8, TNF-α, CRP, etc.), and/or (c) high blood pressure. In other embodiments, neuromodulation treatment can be used to increase heart rate variability or decrease MSBP in patients.

In one embodiment, a patient having extreme or chronic psychological/mental stress in response to an adverse life event or condition and presenting with one or more acute stress indicators or other indicators, such as pre-hypertension (e.g., systolic BP of 120-139 mmHg/diastolic BP of 80-89 mmHg), hypertension (e.g., systolic BP>140 mmHg/diastolic BP>90 mmHg), increased serum levels of IL-6 or CRP, higher levels of glucocorticoid (e.g., cortisol), higher CAR, higher MSBP, decreased heart rate variability, or having other factors presenting an increased risk of developing an eating disorder (e.g., persons having experienced a traumatic brain injury, having experienced traumatic events, adverse childhood, family history of mental illness, eating disorder-associated genetic polymorphisms, etc.) can be treated with renal neuromodulation to reduce a level of renal sympathetic drive and/or reduce a level of systemic norepinephrine spillover in circulating plasma (Schlaich, M. P., et al., *Frontiers in Physiology*, 2012, 3(10): 1-7).

In some embodiments, a patient demonstrating chronic stress indicators for greater than 1 year and presenting with eating disorder symptoms can be diagnosed with an eating disorder by a physician or qualified clinician. In other embodiments, a patient demonstrating chronic stress indicators and eating dysfunction-associated symptoms can present with a qualifying result on an eating disorder screening tool (e.g., tool for assessing an eating disorder diagnosis, tool for assessing an eating disorder risk status, etc.). In further embodiments, chronic psychological stress indicators precipitated by an adverse life condition or event can refer to patients at risk of developing an eating disorder, and patients may be treated with renal neuromodulation to prevent a future on-set of an eating disorder, reduce a risk factor score associated with the severity of an eating disorder, reduce a severity of one or more symptoms associated with an eating disorder, or reduce an incidence of developing one more comorbid conditions/diseases.

Several embodiments of the present technology utilize intravascular devices that reduce sympathetic nerve activity by applying, for example, radiofrequency (RF) energy to target nerve(s) or target site(s) in patients presenting one or more physiological symptoms associated with an eating disorder, or having a risk of developing an eating disorder, such as having one or more eating disorder risk factors. In certain embodiments, neuromodulation is used to reduce renal sympathetic nerve activity in patients having a high risk (e.g., a predisposition or increased likelihood) of developing an eating disorder, one or more signs or symptoms associated with eating disorder development, or, in further embodiments, in patients having been diagnosed with an eating disorder. In a particular embodiment, neuromodulation is used to reduce renal sympathetic nerve activity in patients having an eating disorder risk score (e.g., indicating a status or severity of an eating disorder) above a threshold risk score.

Renal neuromodulation is the partial or complete incapacitation or other effective disruption of the nerves of the kidneys, including nerves terminating in the kidneys or in structures closely associated with the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for preventing incidence of or treating an eating disorder, reducing a severity of an eating disorder, or for alleviating symptoms and other sequelae associated with an eating disorder over longer periods of time, short-term modulation of the renal nerves may also be desirable. For example, some patients may benefit from short-term renal nerve modulation to address acute symptoms presenting during or following an adverse life event or condition, such as hyperarousal, social or other anxiety, PTSD, mood swings, or other stress/eating-related behavioral changes. In particular, some patients may benefit from short-term renal nerve modulation as adjuvant therapy to increase effectiveness of co-administered drugs (e.g., anti-anxiety drugs, antidepressant drugs, anti-psychotic drugs, anti-inflammatory medications (e.g., antihistamines), anti-hypertensive drugs, and sleeping medications (e.g., sedatives) among others administered to support patients), and/or psychotherapy (e.g., cognitive-behavioral therapy, interpersonal therapy, etc.).

Figure 2:
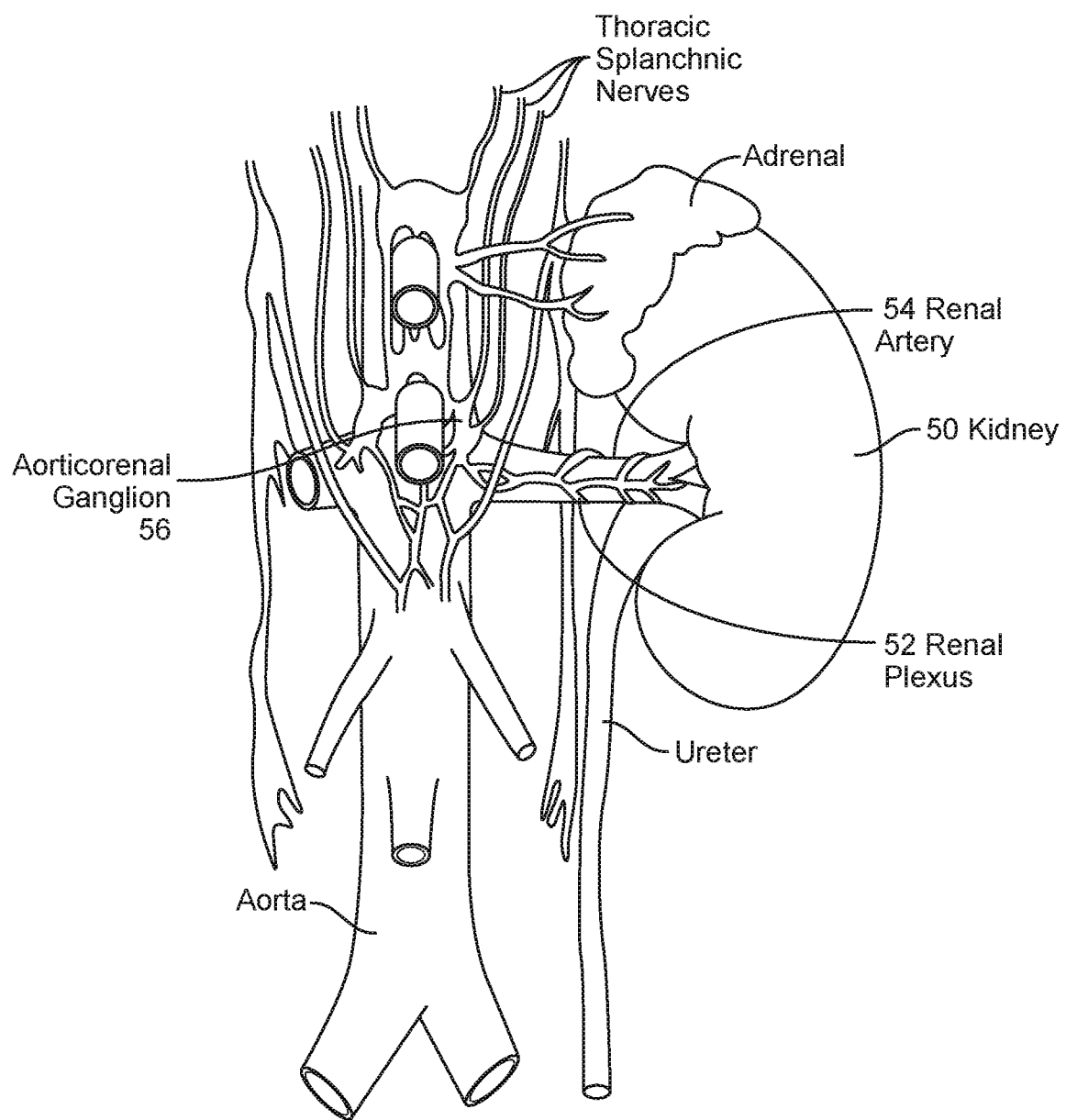
FIG. 2 is an enlarged anatomic view of nerves of a left kidney to form the renal plexus surrounding the left renal artery.

FIG. 2 is an enlarged anatomic view of nerves innervating a left kidney 50 of a patient. As FIG. 2 shows, the kidney 50 is innervated by a renal plexus 52, which is intimately associated with a renal artery 54. The renal plexus 52 is an autonomic plexus that surrounds the renal artery 54 and is embedded within the adventitia of the renal artery 54. The renal plexus 52 extends along the renal artery 54 until it arrives at the substance of the kidney 50, innervating the kidneys while terminating in the blood vessels, the juxtaglomerular apparatus, and the renal tubules (not shown). Fibers contributing to the renal plexus 52 arise from the celiac ganglion (not shown), the superior mesenteric ganglion (not shown), the aorticorenal ganglion 56 and the aortic plexus (not shown). The renal plexus 52, also referred to as the renal nerve, is predominantly comprised of sympathetic components. There is no (or at least very minimal) parasympathetic innervation of the kidney 50.

Preganglionic neuronal cell bodies are located in the intermediolateral cell column of the spinal cord (renal sympathetic nerves arise from T10-L2, FIG. 1). Referring to FIGS. 1 and 2 together, preganglionic axons pass through the paravertebral ganglia (they do not synapse) to become the lesser splanchnic nerve, the least splanchnic nerve, the first lumbar splanchnic nerve, and the second lumbar splanchnic nerve, and they travel to the celiac ganglion (FIG. 1), the superior mesenteric ganglion (FIG. 1), and the aorticorenal ganglion 56 (FIG. 2). Postganglionic neuronal cell bodies exit the celiac ganglion, the superior mesenteric ganglion, and the aorticorenal ganglion 56 to the renal plexus 52 and are distributed to the renal vasculature.

It has previously been shown that stimulation of renal efferent nerves directly affects neural regulation components of renal function that are considerably stimulated in disease states characterized by heightened sympathetic tone such as, for example, increased blood pressure in hypertensive patients. As provided herein, renal neuromodulation is likely to be valuable in the treatment of an eating disorder and/or symptoms associated with an eating disorder. Renal neuromodulation is also likely to be valuable in the prevention of developing an eating disorder in certain at-risk individuals (e.g., individuals having experienced adverse life events or circumstances and/or presenting one or more chronic stress indicators or biomarkers indicating a high likelihood of developing an eating disorder).

Renal neuromodulation may also likely to be valuable in the treatment of diseases and conditions that are associated with eating disorders and/or increased SNS tone such as, for example, cardiovascular disease, hypertension, increased blood pressure variability, systemic inflammation, endothelial dysfunction, vascular inflammation, vessel remodeling and/or hardening, atherosclerosis, and metabolic disorders among others. In particular, renal neuromodulation along the renal artery and/or within branches of the renal artery as described in U.S. patent application Ser. No. 14/839,893, filed Aug. 28, 2015 and incorporated herein by reference in its entirety, is expected to reduce renal sympathetic drive in the kidney, thereby reducing the negative impact of SNS activation on aspects of these and other conditions associated with physiological changes that have impact on psychological and cognitive health. As such, renal neuromodulation is also likely to be particularly valuable in patients having one or more clinical conditions characterized by increased overall and particularly renal sympathetic activity, such as cardiovascular disease, hypertension, increased blood pressure variability, low heart rate variability, systemic inflammation, chronic vascular inflammation, endothelial dysfunction, metabolic syndrome, insulin resistance, diabetes, anxiety disorder, and depression among others.

As the reduction of afferent neural signals contributes to the systemic reduction of sympathetic tone/drive, renal neuromodulation might also be useful in preventing an eating disorder. For example, a reduction in central sympathetic drive may reduce and/or improve measurable physiological parameters typically associated with the development of an eating disorder, prior to on-set of core eating disorder symptoms. Alternatively, a reduction in central sympathetic drive may, for example, reduce an elevated heart rate, improved blood pressure, improve heart rate variability, increase blood flow to the brain, reduce cerebrovascular inflammation, reduce systemic inflammation, and/or improve other chronic stress-related symptoms such as depression and symptoms associated with excessive anxiety (e.g., uncontrollable worrying or fear, panic attacks, etc.).

Other psychologically and/or neurologically related conditions, such as, e.g., depression and disabilities associated with excessive anxiety, as well as other conditions presented as comorbid with eating disorders such as, for example, cardiovascular disease, stroke, hypertension, chronic kidney disease, high BMI (e.g., obesity), metabolic disorder (e.g., diabetes) and substance and/or alcohol abuse, may also be treatable or preventable in eating disorder patients using renal neuromodulation. In some instances, therapeutically-effective renal neuromodulation may improve one or more measurable physiological parameters associated with a comorbid disease or condition in the patient without substantially improving the eating disorder in the patient.

Intravascular devices that reduce sympathetic nerve activity by applying, for example, RF energy to a target site in the renal artery have recently been shown to reduce blood pressure in patients with treatment-resistant hypertension. The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in patients with an eating disorder and increased levels of peripheral inflammatory markers, such as IL-6 and CRP, in patients with an eating disorder experiencing a host of inflammatory challenges.

Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others. Recently, intravascular devices that reduce sympathetic nerve activity by applying an energy field to a target site in the renal blood vessel (e.g., via radio frequency (RF) ablation) have been shown to be efficacious in reducing blood pressure, decreasing blood pressure variability, decreasing nocturnal blood pressure, reducing MSBP, improving arterial stiffness and reducing mediators of systemic inflammation in patients with treatment-resistant hypertension.

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of a renal blood vessel (e.g., renal artery, renal arterial branch, renal ostium, renal vein) and adjacent regions of the renal plexus RP, which lay intimately within or adjacent to the adventitia of the renal blood vessel. Some embodiments of the present technology, for example, include electrode-based or transducer-based approaches, which can be used for therapeutically-effective neuromodulation. For example, an energy delivery element (e.g., electrode) can be configured to deliver electrical and/or thermal energy at a treatment site.

By way of theory, targeting both general afferent and efferent renal sympathetic nerves (e.g., via a catheter-based approach, utilizing extracorporeal ultrasound) may cause beneficial effects extending well beyond affecting a severity of an eating disorder or a risk associated with developing an eating disorder, such as reducing a risk of developing hypertension, stroke, cardiovascular disease, obesity, metabolic disorder or other end organ damage. As discussed herein, a correlation between hyperactivity of the SNS and an increased risk of developing an eating disorder and an increased risk in promoting more severe eating disorder symptoms has been implicated. There is now also evidence that an eating disorder and related symptom severity is associated with chronic inflammatory responses and sympathetic activation appears to affect serum levels of peripheral inflammatory markers. Additionally, chronic stress, obesity and other cardiovascular maladies promote hyperactivity (e.g., overactivity) of the sympathetic nervous system throughout the body. For example, when experiencing stress, including chronic stress, hormonal and neural information (e.g., sensory afferent input) is received by the CNS, which in turn further elevates sympathetic tone via efferent signaling throughout the body. Some aspects of methods of treating patients having an eating disorder or having one or more risk factors, including a high risk score, for the development of an eating disorder, using sympathetic neuromodulation are at least in part derived from the recognition described herein that the kidneys may contribute to elevated central sympathetic drive.

Several aspects of the current technology are configured to reduce renal sympathetic nerve activity within or near the kidney(s) to reduce localized release of norepinephrine. Several properties of the renal vasculature may inform the design of treatment devices and associated methods for achieving target sympathetic neuromodulation, for example, via intravascular access, and impose specific design requirements for such devices. Specific design requirements for renal neuromodulation may include accessing the renal artery, a ureter, a renal pelvis, a major renal calyx, a minor renal calyx, and/or another suitable structure; facilitating stable contact between the energy delivery elements of such devices and a luminal surface or wall of the suitable targeted structure, and/or effectively modulating the renal nerves with the neuromodulatory apparatus.

Intravascular devices that reduce sympathetic nerve activity by applying, for example, RF energy to a treatment site in the renal artery have recently been shown to reduce renal sympathetic drive, renal norepinephrine spillover, and whole body norepinephrine spillover. Renal neuromodulation is expected to reduce renal sympathetic neural activity, and since the reduction of afferent neural signals contributes to the systemic reduction of sympathetic tone/drive, renal neuromodulation is a useful technique in addressing certain risk factors and symptoms associated with an eating disorder that are attributable to systemic sympathetic hyperactivity. For example, as previously discussed, a reduction in central sympathetic drive may treat an eating disorder including reducing a severity of one or more symptoms associated with an eating disorder, reduce a likelihood of developing an eating disorder, as well as improve other comorbid disease manifestations (e.g., hypertension, cardiovascular disease, stroke, metabolic disorders, insulin resistance, diabetes, systemic inflammation, depression, etc.) associated with sympathetic hyperactivity.

Accordingly, renal neuromodulation is expected to be useful in treating an eating disorder, reducing a severity of one or more symptoms in patients afflicted with an eating disorder, preventing and/or treating one or more comorbid conditions or diseases associated with an eating disorder or preventing an incidence of developing an eating disorder in patients presenting certain risk factors. The beneficial effect of renal neuromodulation with respect to a risk associated with development of an eating disorder is expected to apply to patients who do not currently meet the diagnostic standard for an eating disorder diagnosis (e.g., under DSM-5), for example, regardless of the baseline renal sympathetic neural activity or the baseline level of norepinephrine in plasma (e.g., whole body norepinephrine spillover). For example, renal neuromodulation in accordance with embodiments of the present technology can improve one or more measurable physiological parameters corresponding to an eating disorder risk factor or status (e.g., level of severity of diagnosis) in the patient when baseline renal sympathetic neural activity is normal, below normal, or above normal (e.g., hyperactive or overactive). Likewise, renal neuromodulation in accordance with additional embodiments of the present technology can improve one or more measurable physiological parameters corresponding to an eating disorder risk factor or an eating disorder status (e.g., level of severity of diagnosis) in the patient when baseline central sympathetic drive, baseline norepinephrine spillover in plasma, and/or whole body norepinephrine spillover is normal, below normal, or above normal (e.g., hyperactive or overactive). Such an improvement in one or more measurable physiological parameters corresponding to an eating disorder risk factor or an eating disorder status (e.g., level of severity of diagnosis) in the patient can reduce a risk associated with developing an eating disorder in that patient or can reduce symptom severity and/or effectively treat an afflicted patient diagnosed with an eating disorder.

III. METHODS FOR TREATING EATING DISORDERS AND/OR REDUCING A RISK ASSOCIATED WITH DEVELOPING AN EATING DISORDER AND RELATED CONDITIONS

Disclosed herein are several embodiments of methods directed to treating an incidence of an eating disorder in a patient using catheter-based renal neuromodulation. Further embodiments disclosed herein are directed to preventing an incidence of an eating disorder and/or other conditions associated with an increased risk of developing an eating disorder in a patient using catheter-based renal neuromodulation. The methods disclosed herein may represent various advantages over a number of conventional approaches and techniques in that they allow for the potential targeting of elevated sympathetic drive, which may either be a cause of several neurological, immune vascular, or other physiological risk factors associated with an eating disorder or a key mediator of the disorder manifestation. Also, the disclosed methods provide for localized treatment and limited duration treatment regimens (e.g., one-time treatment), thereby reducing patient long-term treatment compliance issues.

In certain embodiments, the methods provided herein comprise performing renal neuromodulation, thereby decreasing sympathetic renal nerve activity, for example, for the purposes of being able to provide one or more of a reduction in a number of eating disorder risk factors, a reduction in severity of one or more eating disorder risk factors, a reduction in a calculated eating disorder risk score, a reversal in vascular damage facilitated by sympathetic activity, or a reduction in systemic inflammation. For example, renal neuromodulation is expected to reduce a level of central sympathetic activity that may contribute to one more underlying causes of eating disorders.

Renal neuromodulation may be repeated one or more times at various intervals until a desired sympathetic nerve activity level or another therapeutic benchmark is reached. In one embodiment, for example, a decrease in sympathetic nerve activity may be observed via a marker of sympathetic nerve activity in patients, such as decreased levels of plasma norepinephrine (noradrenaline), changes in levels of systemic renin in plasma, changes in levels of angiotensin II in plasma, and/or changes in levels of systemic aldosterone in plasma. Other measures or markers of sympathetic nerve activity can include MSNA, norepinephrine spillover, and/or heart rate variability. In some instances, a decrease in SNS activity can be observed as a decrease in norepinephrine and metabolites thereof (e.g., vanillomandelic acid (VMA)) in urine. In another embodiment, other measurable physiological parameters or markers, such as improved baroreceptor sensitivity, improved heart rate responses to stimuli/stress, improved heart rate variability, improved skin conductance, improved blood pressure control (e.g., lower blood pressure), improved blood pressure variability (e.g., improved MSBP, improved nocturnal blood pressure "dipping"), lower levels of peripheral inflammatory biomarkers (e.g., IL-6, IL-8, TNF-α, CRP, etc.), improved levels of NPY, reduced cortisol levels, reduced CAR, reduced glucocorticoid resistance, improved brain neural activity (e.g., in the hippocampus and other brain regions), changes in aldosterone-to-renin ratio (ARR), changes in a salt suppression test, changes in blood plasma levels of potassium, improved blood glucose regulation, etc., can be used to assess efficacy of the thermal modulation treatment for patients diagnosed as having an eating disorder or for patients having one or more risk factors for developing an eating disorder, and/or having a calculated eating disorder risk score above a threshold eating disorder risk score. In certain embodiments, renal neuromodulation may be repeated one or more times at various intervals until a desired sympathetic nerve activity level or another therapeutic benchmark is reached for such patients.

In certain embodiments of the methods provided herein, renal neuromodulation is expected to result in a change in sympathetic nerve activity and/or in other measurable physiological parameters or markers, over a specific timeframe. For example, in certain of these embodiments, sympathetic nerve activity levels are decreased over an extended timeframe, e.g., within 1 month, 2 months, 3 months, 6 months, 9 months or 12 months post-neuromodulation.

In several embodiments, the methods disclosed herein may comprise an additional step of measuring sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure. In certain embodiments, a baseline sympathetic nerve activity level is derived from the subject undergoing treatment. For example, baseline sympathetic nerve activity level may be measured in the subject at one or more timepoints prior to treatment. A baseline sympathetic nerve activity value may represent sympathetic nerve activity at a specific timepoint before neuromodulation, or it may represent an average activity level at two or more timepoints prior to neuromodulation. In certain embodiments, the baseline value is based on sympathetic nerve activity immediately prior to treatment (e.g., after the subject has already been catheterized). Alternatively, a baseline value may be derived from a standard value for sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months, 12 months or 24 months post-neuromodulation.

In certain embodiments of the methods provided herein, the methods are designed to decrease sympathetic nerve activity to a target level. In these embodiments, the methods include a step of measuring sympathetic nerve activity levels post-neuromodulation (e.g., 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease sympathetic nerve activity below a baseline level without requiring a particular target activity level.

In one embodiment, measured norepinephrine content (e.g., assessed via tissue biopsy, assessed in real-time via intravascular blood collection techniques, assessed in real-time via urine, etc.) can be reduced (e.g., at least about 5%, 10%, 20% or by at least 40%) in the patient within, for example, about three months after at least partially inhibiting sympathetic neural activity in nerves proximate a renal blood vessel.

In one embodiment, renal neuromodulation may be performed on a patient having one or more risk factors or symptoms associated with an eating disorder to improve the physiological state of at least one of the eating disorder risk factors. In some embodiments, for example, renal neuromodulation may result in a reduction in a patient's heart rate under stress, may raise heart rate variability, lower a MSBP, lower a nocturnal blood pressure level, reduce systolic blood pressure, reduce blood pressure variability, increase baroreceptor sensitivity, lower skin conductance, reduce a serum level of an inflammatory biomarker, or reduce a level of insulin resistance. In a particular example, a patient having an eating disorder and decreased heart rate variability (e.g., SDNN<50 ms) may have heart rate variability within a normal range (e.g., SDNN>50 ms) after a neuromodulation procedure. In a further example, a reduction in MSBP can be, for example, by at least about 5%, 10% or a greater amount as determined by average ambulatory blood pressure analysis before and after (e.g., 1, 3, 6, or 12 months after) a renal neuromodulation procedure. Likewise, and in yet a further example, a reduction in nocturnal blood pressure level can be, for example, by at least about 5%, 10%, or a greater amount as determined by average ambulatory blood pressure analysis before and after (e.g., 1, 3, 6, or 12 months after) a renal neuromodulation procedure.

In the case of systemic inflammation and/or a patient having elevated serum levels of inflammatory biomarkers, IL-6, IL-8, TNF-α and/or CRP, renal neuromodulation may improve (e.g., reduce a level of) markers of inflammation (e.g., IL-6, IL-8, TNF-α, CRP), and in some embodiments, provide a reduction in biomarker level, for example, by about 5%, 10%, 25%, 45% or a greater amount as determined by blood analysis before and after (e.g., 1, 3, 6, or 12 months after) a renal neuromodulation procedure. In an example where the patient has elevated cortisol levels, elevated CRH levels, and/or glucocorticoid resistance, renal neuromodulation may improve (e.g., reduce a level of) cortisol levels, CRH levels, and/or glucocorticoid resistance by about 5%, about 10%, about 20% or greater amount as determined by quantitative analysis (e.g., dexamethasone binding assay, dexamethasone suppression test, radioimmunoassay, CRH stimulation test, etc.). In other embodiments, and in particular afflicted patients, renal neuromodulation may increase arteriole blood flow, reduce a level of atherosclerosis, or reduce a degree of arterial stiffening in the patient by about 5%, 10% or a greater amount as determined by qualitative or quantitative analysis (e.g., computerized tomography (CT) scan, pulse wave velocity (PWV) analysis, angiography, etc.) before and after (e.g., 1, 3, 6, or 12 months after) a renal neuromodulation procedure.

In another embodiment, renal neuromodulation may be performed on a patient having a calculated eating disorder risk score associated with an eating disorder status in the patient that is above a threshold eating disorder risk score. Renal neuromodulation is expected to therapeutically improve the patient's eating disorder risk score and thereby reduce, diminish, reverse or eliminate the eating disorder in the patient. In one embodiment, a threshold eating disorder risk score may be a theoretical risk score (e.g., based on population studies) that represents a cut-off score for an eating disorder diagnosis. In other embodiments, the threshold eating disorder risk score may be a theoretical risk score that represents an upper limit of acceptable severity and/or acceptable risk of developing an eating disorder.

In a particular example, a patient may be assessed for a number of factors that have been previously determined to validate an eating disorder diagnosis and/or to carry risk for the development of an eating disorder (e.g., number or severity of core eating disorder symptoms, genetic/epigenetic factors, number or duration of adverse life events or circumstances the patient has experienced, number of prior traumatic events the patient experienced, prior brain injury, presence of abuse or neglect during childhood, presence of personal or family history of eating disorders, depression or mental illness, history of anxiety disorder, low heart rate variability, elevated cortisol levels, elevated CAR, low NPY levels, baroreceptor sensitivity, blood pressure, MSBP levels, nocturnal blood pressure levels, MSNA levels, body mass index, substance abuse/habits, etc.). Using an eating disorder risk score calculator tool (e.g., based on epidemiological data), a patient's risk score can be assessed. For patients having a calculated eating disorder risk score above the threshold eating disorder risk score (e.g., signifying an undesirable level of symptom or disorder severity or probability of having an eating disorder), a renal neuromodulation procedure is performed. Renal neuromodulation may improve (e.g., lower, reverse, reduce a rate of increase over time, etc.) the patient's eating disorder risk score. For example, following a renal neuromodulation procedure, a patient's calculated eating disorder risk score may reduce (e.g., improve) by about by about 5%, about 10%, about 15%, about 20%, about 25%, about 30%, about 40%, about 50%, about 75%, or a greater amount as determined by the eating disorder risk score calculator tool. Such improvements in a patient's eating disorder risk score may be detected, for example 1, 3, 6, 12, or 24 months after a renal neuromodulation procedure. In certain embodiments, a threshold risk score can be variable depending on a number of factors including gender, age, socioeconomic levels, geographical residence, etc. For example, a threshold risk score for a male patient can be greater than a threshold risk score for a female patient.

In addition to (or instead of) affecting one or more measurable risk factors associated with an eating disorder or the development of an eating disorder, renal neuromodulation may efficaciously treat one or more measurable physiological parameter(s) or sequela(e) corresponding to the progression or severity of an eating disorder in the patient. For example, in some embodiments, renal neuromodulation may result in an improvement (e.g., prevent further decline, maintain, or improve) in a patient's cognitive abilities and/or emotional/social functioning abilities as assessed by one or more accepted diagnostic test methods (e.g., screening tools, questionnaires, etc.) for identifying eating disorder risk, severity and diagnosis (e.g., PSQI, ESS, ISDI, MEQ, HADS, PHQ-ADS, a VAS, MSLT and/or a polysomnography, etc.). In a specific embodiment, a patient may improve an eating disorder screening test score, maintain an eating disorder screening test score, or decrease a rate of decline (e.g., rate of eating disorder progression) in a test score over time following a renal neuromodulation procedure. Such improvements in a patient's cognitive abilities and/or emotional/social functioning abilities may be detected, for example 1, 3, 6, or 12 months after a renal neuromodulation procedure. In other embodiments, improvements are detected 2, 3, 4, 5 or 10 years after a renal neuromodulation procedure. In some embodiments, an eating diagnostic test score can be improved by about 5%, about 10%, about 15%, about 20%, about 30%, about 40%, about 50%, or about 75%. In other embodiments, patients may report that daily activities are easier following a neuromodulation procedure.

In an example, renal neuromodulation may efficaciously treat one or more aspects of eating disorder indications associated with an eating disorder in the patient. For example, a patient may have an improvement (e.g., a reduction) in the number, the type and/or the duration of eating disorder indications (e.g., frequency of food restriction, number of times patient purged following eating, number of binge-eating episodes, etc.) following a renal neuromodulation procedure. Such improvements in a patient's eating disorder indications may be detected, for example 1, 3, 6, or 12 months after a renal neuromodulation procedure. In other embodiments, improvements are detected 2 or 3 years after a renal neuromodulation procedure. In some embodiments, the patient's eating disorder indications can be improved by about 5%, about 10%, about 15%, about 20%, about 30%, about 40%, about 50%, or about 75% within 3 to 12 months or within 3 to 6 months following a renal neuromodulation procedure.

In a further example, renal neuromodulation may efficaciously treat additional aspects of eating disorder symptoms in the patient. For example, a patient may have an improvement (e.g., a reduction) in the number of instances, the type, and/or the severity of eating disorder indications, such as binge-eating, purging, thinking about body weight or shape, disrupted sleep patterns or poor sleep quality, irritability, excessive anxiety and worry, depression-related symptoms (e.g., sadness, loss of hope, etc.) following a renal neuromodulation procedure. Such improvements in a patient's eating disorder symptoms may be detected, for example, 1, 3, 6, or 12 months after a renal neuromodulation procedure. In other embodiments, improvements are detected 2 or 3 years after a renal neuromodulation procedure. In some embodiments, the level of eating disorder symptoms (e.g., level of severity, number of eating disorder symptoms, the number of days the patient experiences eating disorder symptoms within a logged time period, etc.) can be improved by about 5%, about 10%, about 15%, about 20%, about 30%, about 40%, about 50%, or about 75% within, for example, 3 to 12 months or within 3 to 6 months following a renal neuromodulation procedure. In some embodiments, the patient can experience complete regression or full recovery from the eating disorder symptoms.

Renal neuromodulation may prevent or reduce an incidence of developing one or more comorbid conditions or diseases in a patient with an eating disorder. For example a patient with an eating disorder treated with renal neuromodulation may have a decreased likelihood of developing pre-hypertension, hypertension, cardiovascular disease, stroke risk, metabolic disorders, insulin resistance, diabetes, systemic inflammation, chronic kidney disease, peripheral artery disease, dementia, or infertility, etc. In other embodiments, a patient with an eating disorder treated with renal neuromodulation may have a decreased likelihood of developing depression, an anxiety disorder or other mental disorder. In another embodiment, patients with an eating disorder having one or more comorbid conditions or diseases may have an improvement in (e.g., reduction, maintain a level, slow a rate of progression of) in the one or more comorbid conditions or diseases and associated symptoms thereof. In a particular example, a pre-hypertensive patient (e.g., systolic BP of 120-139 mmHg/diastolic BP of 80-89 mmHg) may have blood pressure below the pre-hypertensive range after a renal neuromodulation procedure. Likewise, a hypertensive patient (e.g., systolic BP>140 mmHg/diastolic BP>90 mmHg) may have blood pressure below the hypertensive range after a renal neuromodulation procedure. Corresponding results may be obtained with angiotensin II levels, plasma aldosterone concentration, plasma renin activity, and/or aldosterone-to-renin ratio. For example, a reduction in an aldosterone-to-renin ratio can be, for example, by at least about 5%, 10% or a greater amount (e.g., about 50%, about 80%, about 90%) as determined by blood analysis and calculation before and after (e.g., 1, 3, 6, or 12 months after) a renal neuromodulation procedure.

Other measurable physiological parameters may also improve following renal neuromodulation. For example, a patient may have an improvement in (e.g., reduction, maintain a level of, slow a rate of progression of) atherosclerosis of extracranial and/or intracranial arteries, clinical measurements of aortic and large-artery, small-vessel disease or other alterations in small arteries providing physiological blood flow, neural activity (e.g., in the amygdala, ventromedial prefrontal cortex, dorsal anterior cingulate cortex, hippocampus and/or insular cortex or other regions involved in the limbic system), following a renal neuromodulation procedure as determined by qualitative or quantitative analysis (e.g., CT scan, PWV analysis, angiography, MM, PET scan, etc.) before and after (e.g., 1, 3, 6, or 12 months after; 2, 3, 4, 5 or 10 years after) a renal neuromodulation procedure.

As discussed previously, the development of an eating disorder in certain individuals may be related to sympathetic overactivity either before (e.g., chronic or episodic), during (e.g., at the time of), or following an adverse life event or circumstance, and, correspondingly, the degree of sympathoexcitation in a patient may be related to one or more of the severity of the clinical presentation of an eating disorder, the number of traumatic events experienced by the patient, whether the patient has had adversity during childhood, number and duration of adverse life events or circumstances (e.g., triggering psychological stress responses), personal or family history of eating disorders, depression or mental illness, history of cardiovascular disease or stroke, among other psychological, physiological and genetic/epigenetic factors. The kidneys are positioned to be both a cause (via afferent nerve fibers) and a target (via efferent sympathetic nerves) of elevated central sympathetic drive. In some embodiments, renal neuromodulation can be used to reduce central sympathetic drive in a patient demonstrating one or more risk factors for an eating disorder in a manner that treats the patient for an eating disorder and/or to prevent an incidence of an eating disorder in the patient in later life. In some embodiments, for example, MSNA can be reduced by at least about 10% in the patient within about three months after at least partially inhibiting sympathetic neural activity in nerves proximate a renal artery of the kidney. Similarly, in some instances whole body norepinephrine spillover to plasma can be reduced at least about 20%, about 30%, about 40%, about 45%, about 50% or a greater amount in the patient within about three months to about 12 months after at least partially inhibiting sympathetic neural activity in nerves proximate a renal artery of the kidney. Additionally, measured norepinephrine content (e.g., assessed via renal biopsy, assessed in real-time via intravascular blood collection techniques, assessed in real-time via urine, etc.) can be reduced (e.g., at least about 5%, 10%, or by at least 20%) in the patient within about three months after at least partially inhibiting sympathetic neural activity in nerves proximate a renal artery innervating the kidney.

In one example, a patient having one or more suspected risk factors for an eating disorder and/or the development of an eating disorder can be subjected to a baseline assessment indicating a first set of measurable parameters corresponding to the one or more risk factors. Such parameters can include, for example, levels of central sympathetic drive (e.g., MSNA, whole body norepinephrine spillover), measured norepinephrine content (e.g., assessed via tissue biopsy, plasma or urine), blood pressure, 24-hour blood pressure variability, heart rate variability, baroreceptor sensitivity, heart rate during stress/stimuli, skin conductance, glucocorticoid levels (e.g., in hair, urine, plasma, etc.), glucocorticoid resistance, CAR level, NPY level, CRH level, inflammatory biomarker levels (e.g., IL-6, IL-8, TNF-α, CRP, etc.), cholesterol levels, blood glucose levels, fasting blood insulin levels, measures of insulin sensitivity, body mass index, perceived cognitive functioning level (e.g., self-reporting, third-party reporting, etc.), one or more brain function test scores, and brain/body imaging for vascular remodeling (e.g., arteriole stiffness, arterial blood flow) and/or brain structural alterations (e.g., atrophy, neural activity, etc.). Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment; 2, 3, 4, 5 or 10 years following the treatment), the patient can be subjected to a follow-up assessment. The follow-up assessment can indicate a measurable improvement in one or more physiological parameters corresponding to the one or more suspected risk factors for the eating disorder or the development of an eating disorder.

The methods described herein address the sympathetic excess that is thought to be an underlying factor in eating disorder progression or a central mechanism through which multiple eating disorder risk factors are manifest in patients. Currently, there are no therapies prescribed to address the effects of sympathetic excess in patients suspected of having an eating disorder or a risk of developing an eating disorder. Certain proposed therapies, such as lifestyle alterations (e.g., exercise, diet, alcohol and other substance/drug avoidance, etc.), cognitive behavioral therapy, blood pressure maintenance (e.g., administration of anti-hypertensive therapies), anti-anxiety and/or anti-depression medications, sleep aides and medications, and reduction and/or maintenance of cholesterol have significant limitations including limited efficacy, undesirable side effects and may be subject to adverse or undesirable drug interactions when used in combination. Moreover, use of any drug regimens (e.g., sleep medications, anti-anxiety, antidepressant, anti-hypertensive, cholesterol-lowering, anti-inflammatory, etc.) can have many challenges, including drug contraindications and drug adherence (particularly prior to onset of symptoms). For example, many of these drug regimens may require the patient to remain compliant with the treatment regimen starting in early life (e.g., prior to on-set of a debilitating mental disorder diagnosis) and continue compliance over time. In contrast, neuromodulation can be a one-time or otherwise limited treatment that would be expected to have durable benefits to treat eating disorders, reduce severity of an eating disorder and/or inhibit the long-term potential of developing an eating disorder and thereby achieve a favorable patient outcome.

In some embodiments, patients demonstrating one or more risk factors associated with an eating disorder or the development of an eating disorder and/or have one or more physiological indicators of sympathetic excess (e.g., combined with additional risk factors) can be treated with renal neuromodulation alone. However, in other embodiments, combinations of therapies can be tailored based on specific conditions and eating disorder risk factors in a particular patient. For example, certain patients can be treated with combinations of therapies such as one or more conventional therapies for treating an anxiety disorder or depression, for treating an eating disorders, and/or reducing blood pressure (e.g., anti-hypertensive drug(s)) and treated with one or more neuromodulation treatments. In another example, renal neuromodulation can be combined with cholesterol lowering agents (e.g., statins), anti-inflammatory therapy (e.g., drug(s)), as well as weight loss and lifestyle change recommendations/programs. In certain embodiments, a patient being treated with one or more pharmaceutical drugs for anxiety and/or conditions associated with an eating disorder can be treated with renal neuromodulation to reduce at least one of a number of or a measured dosage of the pharmaceutical drugs administered to the patient.

Treatment of eating disorder risk factors or symptoms and conditions associated with an eating disorder may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

IV. SELECTED EXAMPLES OF NEUROMODULATION MODALITIES

As noted previously, complete or partial neuromodulation of a target renal sympathetic nerve in accordance with embodiments of the present technology can be electrically-induced, thermally-induced, chemically-induced, or induced in another suitable manner or combination of manners at one or more suitable locations along one or more renal blood vessels during a treatment procedure. For example, neuromodulation may be achieved using various modalities, including for example monopolar or bipolar RF energy, pulsed RF energy, microwave energy, laser light or optical energy, magnetic energy, ultrasound energy (e.g., intravascularly delivered ultrasound, extracorporeal ultrasound, high-intensity focused ultrasound (HIFU)), direct heat energy, radiation (e.g., infrared, visible, gamma), or cryotherapeutic energy, chemicals (e.g., drugs or other agents), or combinations thereof. Where a system uses a monopolar configuration, a return electrode or ground patch fixed externally on the subject can be used. In certain embodiments, neuromodulation may utilize one or more devices including, for example, catheter devices such as the Symplicity Spyral™ catheter (Medtronic plc). Other suitable thermal devices are described in U.S. Pat. Nos. 7,653,438, 8,347,891, and U.S. patent application Ser. No. 13/279,205, filed Oct. 21, 2011. Other suitable devices and technologies are described in U.S. patent application Ser. No. 13/279,330, filed Oct. 23, 2011, International Patent Application No. PCT/US2015/021835, filed Mar. 20, 2015, and International Patent Application No. PCT/US2015/013029, filed Jan. 27, 2015. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and U.S. Pat. No. 8,888,773. Other examples of suitable direct heat devices are described in International Patent Application No. PCT/US2014/023738 filed Mar. 11, 2014, and U.S. patent application Ser. No. 14/203,933, filed Mar. 11, 2014. All of the foregoing patent references are incorporated herein by reference in their entireties.

In those embodiments of the methods disclosed herein that utilize partial ablation, the level of energy delivered to the target artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities. In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial neuromodulation of a renal sympathetic nerve can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic nerve can slow or potentially block conduction of neural signals to produce a prolonged or permanent reduction in sympathetic activity. A variety of suitable types of energy, such as those mentioned above, can be used to stimulate and/or heat tissue at a treatment location. In some embodiments, neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective neuromodulation of a target sympathetic nerve. For example, cryotherapeutic treatment can include cooling tissue at a treatment location in a manner that modulates neural function. For example, sufficiently cooling at least a portion of a target sympathetic nerve can slow or potentially block conduction of neural signals to produce a prolonged or permanent reduction in sympathetic activity associated with the target sympathetic nerve. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion.

Neuromodulation using a cryotherapeutic treatment in accordance with embodiments of the present technology can include cooling a structure proximate an inner surface of a vessel or chamber wall such that tissue is effectively cooled to a depth where sympathetic nerves reside. For example, a cooling assembly of a cryotherapeutic device can be cooled to the extent that it causes therapeutically-effective, cryogenic neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause organs and tissues to rise and fall and thereby move the arteries and other structures associated with these organs and tissues. In addition, blood flow is pulsatile and can cause structures associated with the kidneys to pulse. Cryogenic adhesion also can facilitate intravascular or intraluminal positioning, particularly in relatively-small structures (e.g., renal branch arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In certain embodiments, monitoring, assessing and/or determining neuromodulation efficacy can be accomplished by detecting changes in the level of one or more surrogate biomarkers (e.g., a biomarker that directly or indirectly correlates with sympathetic nerve activity in the patient, a biomarker that directly or indirectly correlates with hypertension, arterial stiffness and/or an inflammatory response in the patient) in serum, plasma and/or urine in response to neuromodulation. Systems and method for monitoring the efficacy of neuromodulation by measuring the levels of one or more biomarkers associated with neuromodulation including, for example, proteins or non-protein molecules that exhibit an increase or decrease in level or activity in response to neuromodulation are described in, e.g., International Patent Application No. PCT/US2013/030041, filed Mar. 8, 2013, and International Patent Application No. PCT/US2015/047568, filed Aug. 28, 2015, the disclosures of which are incorporated herein by reference in their entireties. In other embodiments, measured levels of protein or non-protein molecules (e.g., associated with norepinephrine spillover, associated with inflammatory responses, etc.) that exhibit an increase or decrease in level or activity in response to targeted neuromodulation can be assessed pre- and post-neuromodulation in tissue biopsies.

V. SELECTED EMBODIMENTS OF RENAL NEUROMODULATION SYSTEMS AND DEVICES

Figure 3:
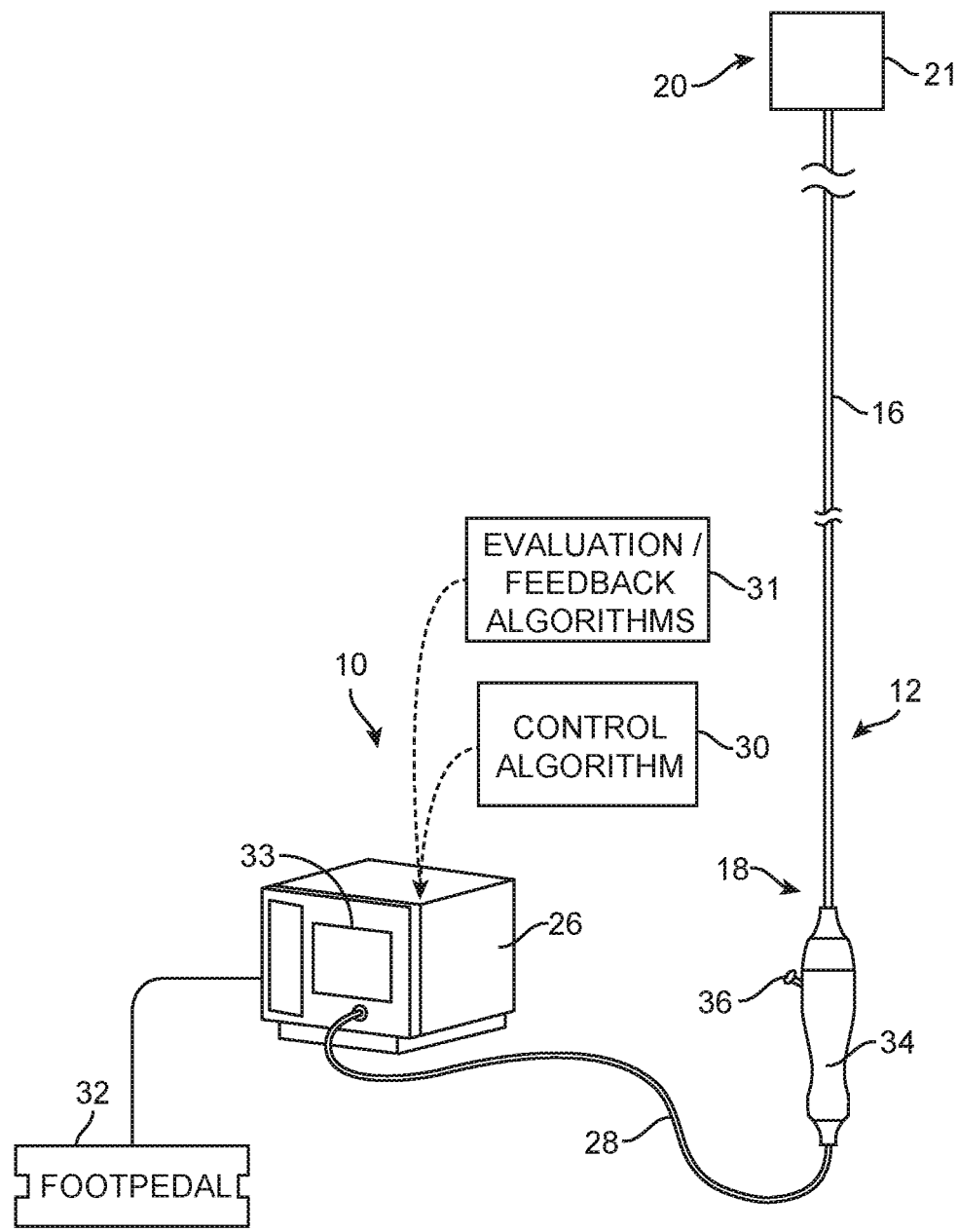
FIG. 3 illustrates an intravascular neuromodulation system configured in accordance with an embodiment of the present technology.

FIG. 3 illustrates a renal neuromodulation system 10 configured in accordance with an embodiment of the present technology. The system 10, for example, may be used to perform therapeutically-effective renal neuromodulation on a patient (a) to reduce the risk of occurrence of an eating disorder, (b) to reduce a calculated eating disorder risk score corresponding to an eating disorder status, (c) to reduce a severity of neurological symptoms relating to an eating disorder, and/or (d) to treat and/or prevent development of one or more comorbid conditions/diseases associated with an eating disorder (e.g., hypertension, cardiovascular disease, stroke risk, metabolic disorders, insulin resistance, diabetes, systemic inflammation, dementia, chronic kidney disease, etc.). In one embodiment, the patient may be diagnosed with increased overall sympathetic activity, and, in particular, conditions associated with central sympathetic overstimulation and increased risk of developing an eating disorder, such as hypertension, blood pressure variability, systemic inflammation, anxiety, chronic stress, depression, cardiovascular disease, history of stroke or TIA, obesity, metabolic syndrome, insulin resistance and diabetes, among others.

The system 10 includes an intravascular treatment device 12 operably coupled to an energy source or console 26 (e.g., a RF energy generator, a cryotherapy console). In the embodiment shown in FIG. 3, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can be configured to ablate nerve tissue and/or for monitoring one or more physiological parameters within the vasculature. Accordingly, a neuromodulation assembly 21 suitable for ablation may include one or more electrodes, transducers, energy-delivery elements or cryotherapeutic cooling assemblies. Neuromodulation assemblies 21 suitable for monitoring may also include a nerve monitoring device and/or blood collection/analysis device. In some embodiments, the neuromodulation assembly 21 can be configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In further embodiments, the neuromodulation assembly 21 can include one or more electrodes configured to deliver ablation energy and/or stimulation energy. In some arrangements, the neuromodulation assembly 21 can include one or more sensor(s) for detecting impedance or nerve monitoring signals. In any of the foregoing embodiments, the neuromodulation assembly 21 may comprise an irrigated electrode.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The console 26 can be configured to deliver the treatment energy via an automated control algorithm 30 and/or under the control of the clinician. In addition, the console 26 may include one or more evaluation and/or feedback algorithms 31 to provide feedback to the clinician before, during, and/or after therapy.

The console 26 can further include a device or monitor that may include processing circuitry, such as a microprocessor, and a display 33. The processing circuitry may be configured to execute stored instructions relating to the control algorithm 30. The console 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or balloon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

VI. SELECTED EXAMPLES OF TREATMENT PROCEDURES FOR RENAL NEUROMODULATION

A. Achieving Intravascular Access to the Renal Artery

Figures 4A, 4B:
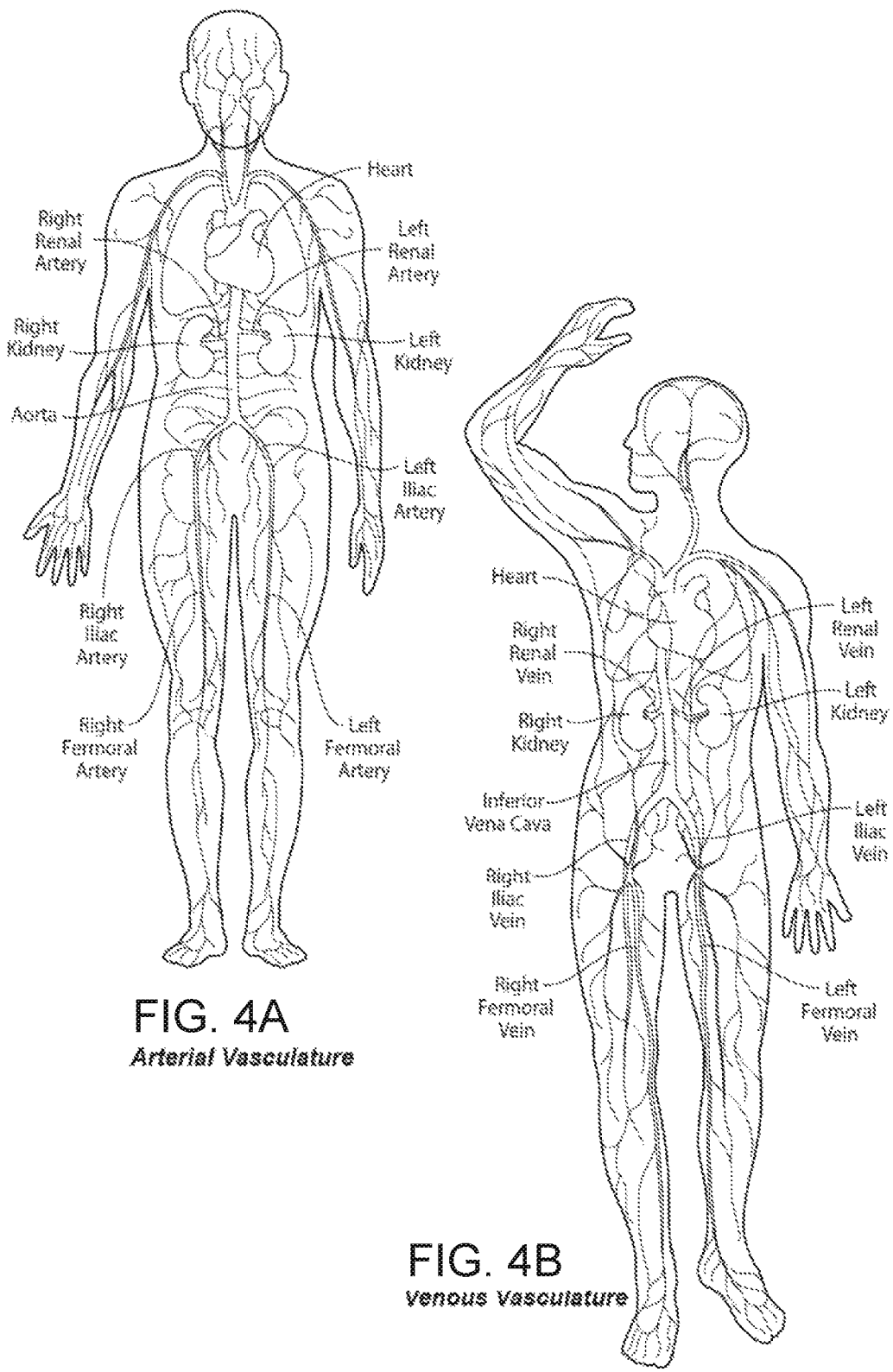
FIGS. 4A and 4B are anatomic views of the arterial vasculature and venous vasculature, respectively, of a human.

In accordance with the present technology, neuromodulation of a left and/or right renal plexus RP, which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This route comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

B. Properties and Characteristics of the Renal Vasculature

Properties and characteristics of the renal vasculature impose challenges to both access and treatment methods, and to system/device designs. Since neuromodulation of a left and/or right renal plexus RP may be achieved in accordance with embodiments of the present technology through intravascular access, various aspects of the design of apparatus, systems, and methods for achieving such renal neuromodulation are disclosed herein. Aspects of the technology disclosed herein address additional challenges associated with variation of physiological conditions and architecture across the patient population and/or within a specific patient across time, as well as in response to disease states, such as hypertension, atherosclerosis, vascular disease, chronic inflammatory condition, insulin resistance, diabetes, metabolic syndrome, etc. For example, the design of the intravascular device and treatment protocols can address not only material/mechanical, spatial, fluid dynamic/hemodynamic and/or thermodynamic properties, but also provide particular algorithms and feedback protocols for delivering energy and obtaining real-time confirmatory results of successfully delivering energy to an intended target location in a patient-specific manner.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access can account for these and other aspects of renal arterial anatomy and its variation across the patient population when minimally invasively accessing a renal artery. For example, spiral or helical CT technology can be used to produce 3D images of the vascular features for individual patients, and intravascular path choice as well as device size/diameter, length, flexibility, etc. can be selected based upon the patient's specific vascular features.

In addition to complicating renal arterial access, specifics of the renal anatomy also complicate establishment of stable contact between neuromodulatory apparatus and a luminal surface or wall of a renal blood vessel. When the neuromodulatory apparatus includes an energy delivery element, such as an electrode, transducer, or a cryotherapeutic device, consistent positioning and appropriate contact force applied by the energy or cryotherapy delivery element to the vessel wall, and adhesion between the applicator and the vessel wall can be important for predictability. However, navigation can be impeded by the tight space within a renal artery RA, as well as tortuosity of the artery. Furthermore, establishing consistent contact can be complicated by patient movement, respiration, and/or the cardiac cycle because these factors may cause significant movement of the renal artery RA relative to the aorta, and the cardiac cycle may transiently distend the renal artery RA (i.e., cause the wall of the artery to pulse). To address these challenges, the treatment device or applicator may be designed with relative sizing and flexibility considerations. For example, the renal artery may have an internal diameter in a range of about 2-10 mm and the treatment device can be delivered using a 3, 4, 5, 6, 7 French, or in some cases, an 8 French sized catheter. To address challenges associated with patient and/or arterial movement during treatment, the treatment device and neuromodulation system can be configured to use sensory feedback, such as impedance and temperature, to detect instability and to alert the operator to reposition the device and/or to temporarily stop treatment. In other embodiments, energy delivery algorithms can be varied in real-time to account for changes detected due to patient and/or arterial movement. In further examples, the treatment device may include one or more modifications or movement resistant enhancements such as atraumatic friction knobs or barbs on an outside surface of the device for resisting movement of the device relative to the desired tissue location, positionable balloons for inflating and holding the device in a consistent and stable position during treatment, or the device can include a cryogenic component that can temporarily freeze or adhere the device to the desired tissue location.

After accessing a renal artery and facilitating stable contact between neuromodulatory apparatus and a luminal surface of the artery, nerves in and around the adventitia of the artery can be modulated via the neuromodulatory apparatus. In further embodiments, energy can be applied via the neuromodulatory apparatus to renal perivascular adipose tissue positioned adjacent to the targeted renal artery. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant (e.g., 1-3 mm) from the luminal surface of the artery. Sufficient energy can be delivered to or heat removed from the target renal nerves to modulate the target renal nerves without excessively cooling or heating the vessel wall to the extent that the wall is frozen, desiccated, or otherwise potentially affected to an undesirable extent. For example, when employing energy modalities such as RF or ultrasound, energy delivery can be focused on a location further from the interior vessel wall. In one embodiment, the majority of the RF or ultrasound energy can be focused on a location (e.g., a "hot spot") 1-3 mm beyond the interior surface of the vessel wall. The energy will dissipate from the hot spot in a radially decreasing manner. Thus, the targeted nerves can be modulated without damage to the luminal surface of the vessel. A potential clinical complication associated with excessive heating is thrombus formation from coagulating blood flowing through the artery. Given that this thrombus may cause a kidney infarct, thereby causing irreversible damage to the kidney, thermal treatment from within the renal artery RA can be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery. Accordingly, sensory feedback, such as impedance and temperature, can be used to assess whether a desired energy distribution is administered at the treatment site and can, in some instances, be used to change an energy delivery algorithm in real-time to adjust for varying fluctuations in the properties and conditions affecting heat transfer dynamics at the treatment site.

The neuromodulatory apparatus can also be configured to allow for adjustable positioning and repositioning of an energy delivery element or a cryotherapeutic device, within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the cryotherapeutic devices or energy delivery elements and/or repositioning of the neuromodulatory apparatus to multiple treatment locations may be desirable. It should be noted, however, that a benefit of creating a circumferential lesion or ablation may outweigh the potential of renal artery stenosis or the risk may be mitigated with certain embodiments or in certain patients and creating a circumferential lesion or ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging.

Blood flow through a renal artery may be temporarily occluded for a short time with minimal or no complications. However, occlusion for a significant amount of time can be avoided in some cases to prevent injury to the kidney such as ischemia. It can be beneficial to avoid occlusion altogether or, if occlusion is beneficial, to limit the duration of occlusion, for example to 2-5 minutes.

C. Neuromodulation of Renal Sympathetic Nerve at Treatment Site

Figure 5:
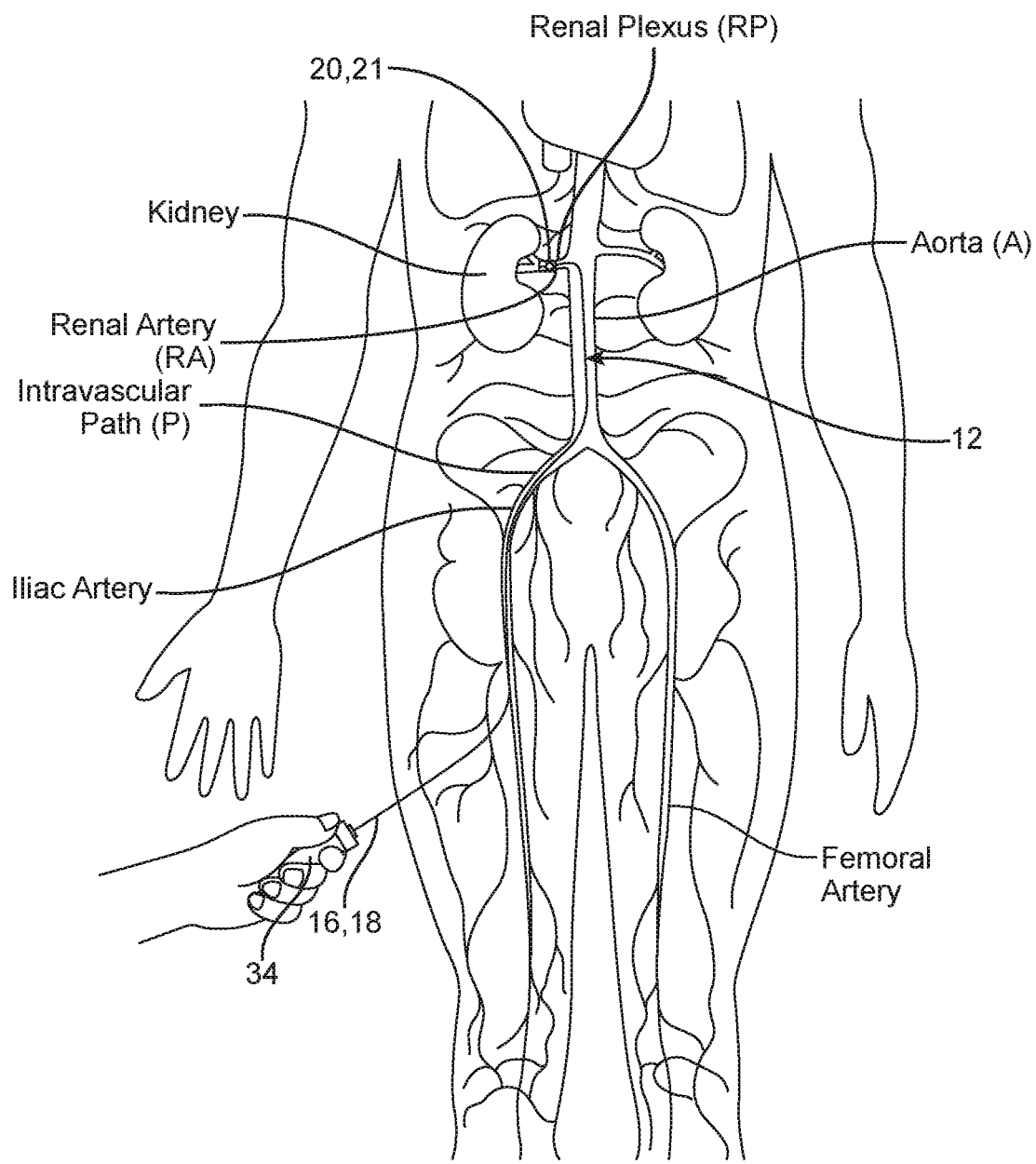
FIG. 5 illustrates modulating renal nerves with a neuromodulation system configured in accordance with an embodiment of the present technology.

FIG. 5 illustrates modulating renal nerves with an embodiment of the system 10 (FIG. 3). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., CT, fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. For example, the application of energy can be applied to renal neural tissue or to renal perivascular adipose tissue that within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP. In targeting the renal perivascular adipose tissue, the effects of the energy delivery may achieve thermal ablation or non-ablative thermal alteration or damage to such cells. While delivery of energy to alter or damage renal perivascular adipose tissue has been discussed, it is also anticipated that other types of cell-altering or damaging therapies (e.g., delivery of chemical agents) can be used.

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured form a partially-circumferential lesion or a fully-circumferential lesion at a single longitudinal segment or zone of the vessel. During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

Furthermore, a treatment procedure can include treatment at any suitable number of treatment locations, e.g., a single treatment location, two treatment locations, or more than two treatment locations. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16 fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

Figure 6:
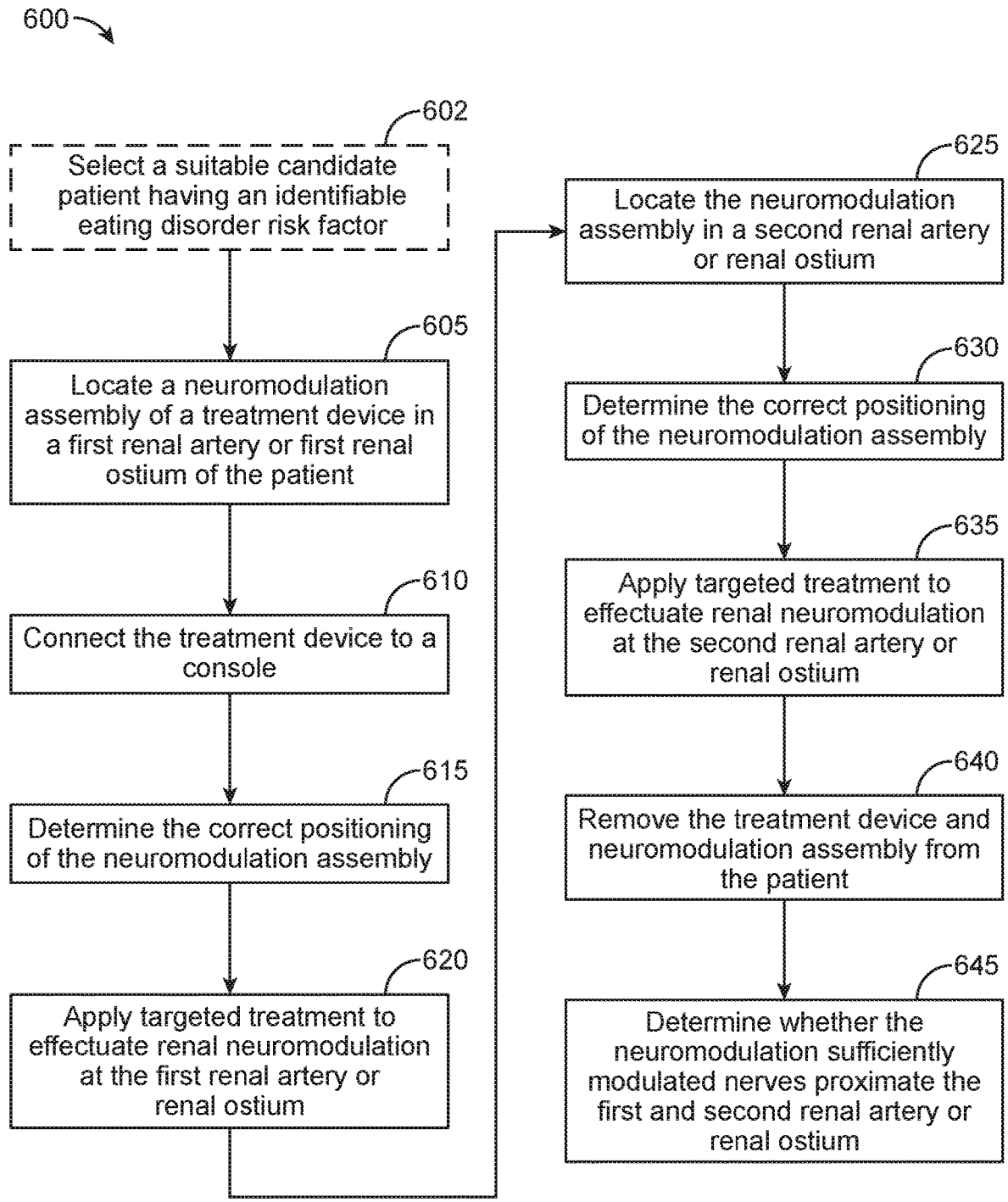
FIG. 6 is a block diagram illustrating a method of modulating renal nerves in accordance with an embodiment of the present technology.

FIG. 6 is a block diagram illustrating a method 600 of modulating renal nerves using the system 10 described above with reference to FIGS. 3 and 5. With reference to FIGS. 3, 5 and 6 together, the method 600 can optionally include selecting a suitable candidate patient having an identifiable eating disorder risk factor for performing renal neuromodulation (block 602). For example, a suitable patient can include a patient having an eating disorder risk score corresponding to an eating disorder status in the patient that is above a threshold level, a patient having one or more measurable risk factors for developing an eating disorder, a patient having one or more identifiable eating disorder symptoms, a patient diagnosed with an eating disorder, an at-risk patient having a history of an eating or other mental disorder (e.g., depression, anxiety disorder) and/or a genetic predisposition for developing an eating disorder, and/or a patient with a history of cardiovascular disease or stroke and having one or more identifiable risk factors for developing an eating disorder.

Modulating SNS nerves innervating the kidneys is expected to lower renal nerve activity and/or central SNS nerve activity, thereby inhibiting, preventing, slowing, disrupting or reversing physiological pathways associated with eating disorders and/or lowering a risk associated with developing an eating disorder in the patient either before or after on-set of one or more eating disorder symptoms. In particular, targeting the renal nerve for neuromodulation is anticipated to reduce renal norepinephrine spillover, whole body norepinephrine spillover, and reduce central sympathetic drive (e.g., reduce a level of efferent SNS nerve firing) in the patient, thereby inhibiting, preventing, slowing, disrupting or reversing an eating disorder and/or symptoms associated with an eating disorder and/or conditions proposed to increase a patient's risk of developing an eating disorder. Further, damaging renal perivascular adipose tissue is anticipated to reduce renal norepinephrine spillover (e.g., released) from these cells. Without being bound by theory, renal neuromodulation is anticipated to address the hyperactivity of the SNS and/or the elevated SNS tone present in patients with an eating disorder and/or patients having one or more risk factors for developing an eating disorder. In other instances, and without being bound by theory, an overactive or hyperactive SNS is believed to be an underlying contributing cause of eating disorders and renal neuromodulation is anticipated to prevent or prohibit the development of a hyperactive or overactive SNS in a patient prior to or subsequent to experiencing an adverse life event or circumstance that precipitates, for example, excessive or chronic psychological stress. In such instances, eating disorders and/or eating disorder symptoms can be attenuated and/or avoided despite experiencing the stress-inducing, adverse life event or circumstance.

The method 600 can include intravascularly locating the neuromodulation assembly 21 in a delivery state (e.g., low-profile configuration) to a first target site in or near a first renal blood vessel (e.g., first renal artery) or first renal ostium (block 605). The treatment device 12 and/or portions thereof (e.g., the neuromodulation assembly 21) can be inserted into a guide catheter or sheath to facilitate intravascular delivery of the neuromodulation assembly 21. In certain embodiments, for example, the treatment device 12 can be configured to fit within an 8 Fr guide catheter or smaller (e.g., 7 Fr, 6 Fr, etc.) to access small peripheral vessels. A guide wire (not shown) can be used to manipulate and enhance control of the shaft 16 and the neuromodulation assembly 21 (e.g., in an OTW or a RX configuration). In some embodiments, radiopaque markers and/or markings on the treatment device 12 and/or the guide wire can facilitate placement of the neuromodulation assembly 21 at the first target site (e.g., a first renal artery or first renal ostium of the patient). In some embodiments, a contrast material can be delivered distally beyond the neuromodulation assembly 21, and fluoroscopy and/or other suitable imaging techniques can be used to aid in placement of the neuromodulation assembly 21 at the first target site.

The method 600 can further include connecting the treatment device 12 to the console 26 (block 610), and determining whether the neuromodulation assembly 21 is in the correct position at the target site and/or whether the neuromodulation assembly (e.g., electrodes or cryotherapy balloon) is functioning properly (block 615). Once the neuromodulation assembly 21 is properly located at the first target site and no malfunctions are detected, the console 26 can be manipulated to initiate application of an energy field to the target site to cause electrically-induced and/or thermally-induced partial or full denervation of the kidney (e.g., using electrodes or cryotherapeutic devices). Accordingly, heating and/or cooling of the neuromodulation assembly 21 causes modulation of renal nerves at the first target site to cause partial or full denervation of the kidney associated with the first target site (block 620).

In one example, the treatment device 12 can be an RF energy emitting device and RF energy can be delivered through energy delivery elements or electrodes to one or more locations along the inner wall of the first renal blood vessel or first renal ostium for predetermined periods of time (e.g., 120 seconds). In some embodiments, multiple treatments (e.g., 4-6) may be administered in both the left and right renal blood vessels (e.g., renal arteries) to achieve a desired coverage and/or desired inhibition of sympathetic neural activity in the body.

In some embodiments, a treatment procedure can include applying a suitable treatment modality at a treatment location in a testing step (not shown) followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

A technical objective of a treatment may be, for example, to heat tissue to a desired depth (e.g., at least about 3 mm) to a temperature that would lesion a nerve (e.g., about 65° C.). A clinical objective of the procedure typically is to treat (e.g., lesion) a sufficient number of renal nerves (either efferent or afferent nerves) to cause a reduction in sympathetic tone or drive to the kidneys. If the technical objective of a treatment is met (e.g., tissue is heated to about 65° C. to a depth of about 3 mm) the probability of forming a lesion of renal nerve tissue is high. The greater the number of technically successful treatments, the greater the probability of modulating a sufficient proportion of renal nerves, and thus the greater the probability of clinical success.

In a specific example of using RF energy for renal nerve modulation, a clinician can commence treatment which causes the control algorithm 30 (FIG. 3) to initiate instructions to the generator (not shown) to gradually adjust its power output to a first power level (e.g., 5 watts) over a first time period (e.g., 15 seconds). The power increase during the first time period is generally linear. As a result, the generator increases its power output at a generally constant rate of power/time. Alternatively, the power increase may be non-linear (e.g., exponential or parabolic) with a variable rate of increase. Once the first power level and the first time are achieved, the algorithm may hold at the first power level until a second predetermined period of time has elapsed (e.g., 3 seconds). At the conclusion of the second period of time, power is again increased by a predetermined increment (e.g., 1 watt) to a second power level over a third predetermined period of time (e.g., 1 second). This power ramp in predetermined increments of about 1 watt over predetermined periods of time may continue until a maximum power $P_{MAX}$ is achieved or some other condition is satisfied. In one embodiment, $P_{MAX}$ is 8 watts. In another embodiment $P_{MAX}$ is 10 watts. Optionally, the power may be maintained at the maximum power $P_{MAX}$ for a desired period of time or up to the desired total treatment time (e.g., up to about 120 seconds).

In another specific example, the treatment device 12 can be a cryogenic device and cryogenic cooling can be applied for one or more cycles (e.g., for 30 second increments, 60 second increments, 90 second increments, etc.) in one or more locations along the circumference and/or length of the first renal artery or first renal ostium. The cooling cycles can be, for example, fixed periods or can be fully or partially dependent on detected temperatures (e.g., temperatures detected by a thermocouple (not shown) of the neuromodulation assembly 21). In some embodiments, a first stage can include cooling tissue until a first target temperature is reached. A second stage can include maintaining cooling for a set period, such as 15-180 seconds (e.g., 90 seconds). A third stage can include terminating or decreasing cooling to allow the tissue to warm to a second target temperature higher than the first target temperature. A fourth stage can include continuing to allow the tissue to warm for a set period, such as 10-120 seconds (e.g., 60 seconds). A fifth stage can include cooling the tissue until the first target temperature (or a different target temperature) is reached. A sixth stage can include maintaining cooling for a set period, such as 15-180 seconds (e.g., 90 seconds). A seventh stage can, for example, include allowing the tissue to warm completely (e.g., to reach a body temperature).

The neuromodulation assembly 21 can then be located at a second target site in or near a second renal blood vessel (e.g., second renal artery) or second renal ostium (block 625), and correct positioning of the assembly 21 can be determined (block 630). In selected embodiments, a contrast material can be delivered distally beyond the neuromodulation assembly 21 and fluoroscopy and/or other suitable imaging techniques can be used to locate the second renal artery. The method 600 continues by applying targeted heat or cold to effectuate renal neuromodulation at the second target site to cause partial or full denervation of the kidney associated with the second target site (block 635).

After providing the therapeutically-effective neuromodulation energy (e.g., cryogenic cooling, RF energy, ultrasound energy, etc.), the method 600 may also include removing the treatment device 12 (e.g., catheter) and the neuromodulation assembly 21 from the patient (block 640). In some embodiments, the neuromodulation assembly 21 can be an implantable device (not shown) and a treatment procedure can include implanting the neuromodulation assembly 21 at a suitable treatment location within the patient. Other treatment procedures for modulation of target sympathetic nerves in accordance with embodiments of the present technology are also possible.

The method 600 may also include determining whether the neuromodulation sufficiently modulated nerves or other neural structures proximate the first and second target sites (block 645). For example, the process of determining whether the neuromodulation therapeutically treated the nerves can include determining whether nerves were sufficiently modulated or otherwise disrupted to reduce, suppress, inhibit, block or otherwise affect the afferent and/or efferent renal signals (e.g., by evaluation of suitable biomarkers, stimulation and recording of nerve signals, etc.). Examples of suitable biomarkers and their detection are described in International Patent Application No. PCT/US2013/030041, filed Mar. 8, 2013, and International Patent Application No. PCT/US2015/047568, filed Aug. 28, 2015, the disclosures of which are incorporated herein by reference in their entireties. Other suitable devices and technologies, such as endovascular intraoperative renal nerve monitoring devices are described in International Patent Application No. PCT/US12/63759, filed Jan. 29, 2013, and incorporated herein by reference in its entirety.

In a further embodiment, patient assessment could include determining whether the neuromodulation therapeutically treated the patient for one or more symptoms associated with an eating disorder, e.g., core eating disorder symptoms (e.g., intense fear of gaining weight or becoming fat, behaviors that interfere with weight gain (e.g., calorie restriction, purging, use of laxatives, etc.), disturbance in the way one sees body weight or shape, eating large amount of food in a discrete amount of time (e.g., within a 2 hour period), sense of lack of control over eating, eating until uncomfortably full, eating large amounts of food when not feeling physically hungry, recurrent compensatory behavior to prevent weight gain (e.g., self-induced vomiting, misuse of laxatives, diuretics, or medications), fasting, excessive exercise, feeling ashamed or disgusted with oneself, or depressed, etc.), feelings of anxiety or depression, systemic inflammation, and undesirable elevations in heart rate, blood pressure, and skin conductance, among others. Assessment of certain suitable biomarkers and/or nerve signals may be made immediately or shortly after neuromodulation (e.g., about 15 minutes, about 24 hours, or about 7 days post-neuromodulation). In further embodiments, patient assessment could be performed at time intervals (e.g., about 1 month, 3 months, 6 months, 12 months) following neuromodulation treatment. For example, the patient can be assessed for measurements of blood pressure, blood pressure variability, nocturnal blood pressure "dipping," MSBP level, skin conductance, resting heart rate, measures of sympathetic activity (e.g., MSNA, renal and/or total body norepinephrine spillover, plasma norepinephrine levels, and heart rate variability), peripheral inflammatory markers (e.g., IL-6, CRP, etc.), NPY level, measures of HPA axis function (e.g., glucocorticoid levels (e.g., in hair, urine, plasma, etc.), glucocorticoid resistance, CAR level, CRH level, etc.), sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio), and/or a post-neuromodulation eating disorder risk score (e.g., via an eating disorder screening tool for determining a severity of an eating disorder).

In other embodiments, various steps in the method 600 can be modified, omitted, and/or additional steps may be added. In further embodiments, the method 600 can have a delay between applying therapeutically-effective neuromodulation energy to a first target site at or near a first renal artery or first renal ostium and applying therapeutically-effective neuromodulation energy to a second target site at or near a second renal artery or second renal ostium. For example, neuromodulation of the first renal artery can take place at a first treatment session, and neuromodulation of the second renal artery can take place at a second treatment session at a later time.

Figure 7:
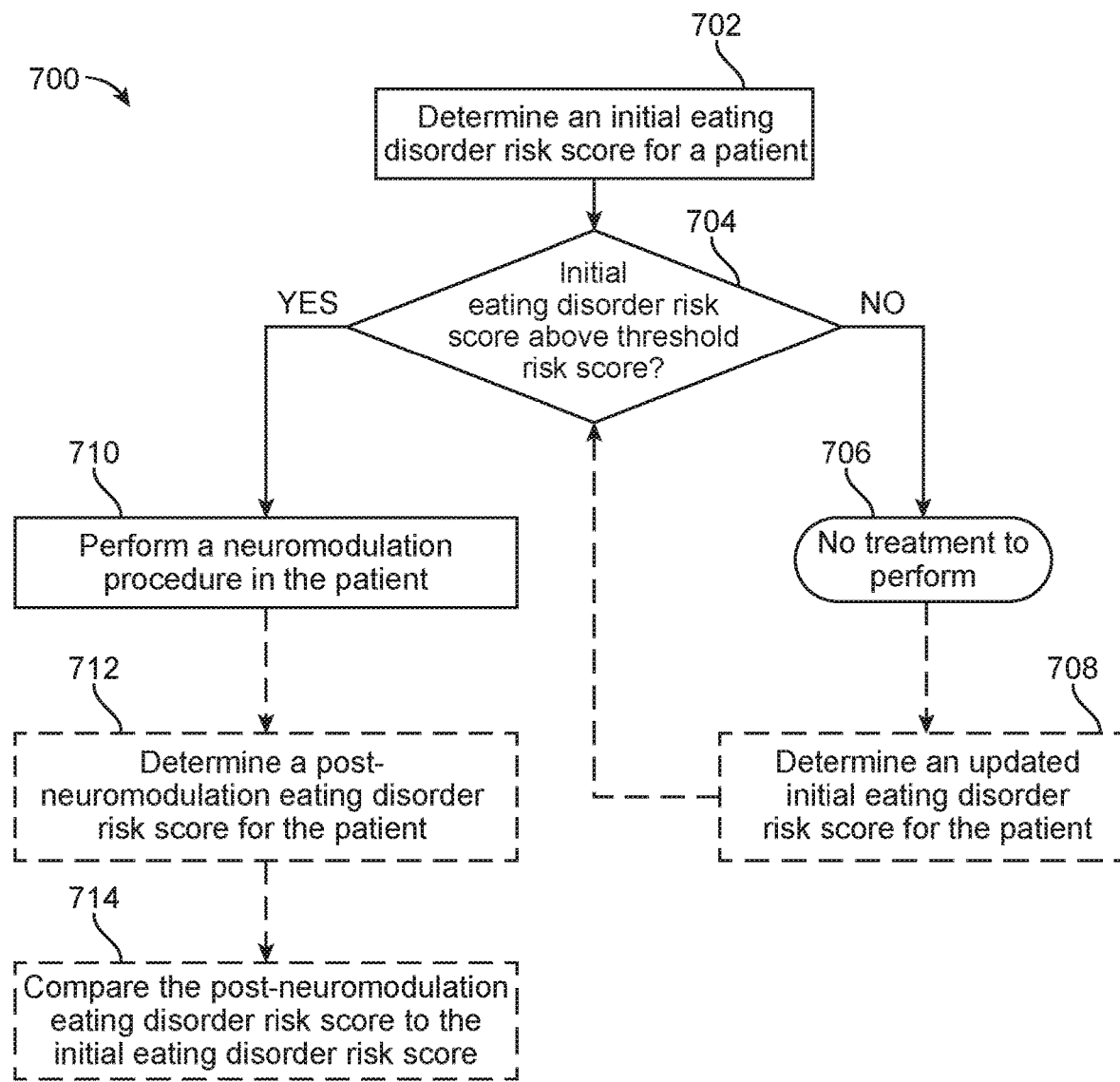
FIG. 7 is a block diagram illustrating a method for improving an eating disorder risk score for a patient in accordance with an embodiment of the present technology.

FIG. 7 is a block diagram illustrating a method 900 for improving an eating disorder risk score for a patient in accordance with aspects of the present technology. In a first step, the method 700 can include determining an initial eating disorder risk score for a patient (block 702). For example, one or more suitable eating disorder risk score calculating techniques or tools can be used to establish an eating disorder risk score corresponding to an eating disorder status in the patient as described above. At decision block 704, the initial eating disorder risk score can be evaluated against a threshold risk score or value. If the initial eating disorder risk score is not above the threshold risk score, there is no need to reduce the eating disorder risk score for the patient at the current time and no treatment is selected to perform (block 706). In such a patient, a clinician may recommend monitoring the patient's eating disorder risk score over time. For example, a clinician can optionally determine an updated initial eating disorder risk score for the patient after a determined time lapse (e.g., 1 month, 2 months, 3 months, 6 months, 12 months, etc.) (block 708). Following each eating disorder risk score evaluation (block 708), the patient's eating disorder risk score is evaluated against the threshold risk score or value (decision block 704).

If the patient's eating disorder risk score from method step 702, or from the optional method step 708, is higher than the threshold risk score, the method 700 can include performing a neuromodulation procedure in the patient (block 710). In one example, the patient can be a suitable candidate patient as identified in method step 602 of method 600 described above, and the neuromodulation procedure can be performed as described in continuing steps of method 600. In other embodiments, a clinician can perform an alternative neuromodulation procedure at method step 710. For example, neuromodulation of other target (e.g., non-renal) sympathetic nerves or neuromodulation in a single renal blood vessel (e.g., renal artery) may be performed on the patient.

The method 700 is expected to improve the patient's eating disorder risk score or reduce a probability of the patient developing an eating disorder. Optionally, the clinician can further determine a post-neuromodulation eating disorder risk score for the patient (block 712). For example, the patient can be evaluated using the eating disorder risk score tool to assess the patient's post-neuromodulation eating disorder status or, alternatively, risk of developing an eating disorder. If the post-neuromodulation eating disorder risk score is determined for the patient in step 712, the method includes comparing the post-neuromodulation eating disorder risk score to the initial eating disorder risk score (block 714). In determining if the method 700 is successful, the post-neuromodulation eating disorder risk score is lower than the patient's initial eating disorder risk score as determined in step 702 (or updated initial eating disorder risk score as determined in step 708). In some examples, the post-neuromodulation eating disorder risk score is lower than the initial eating disorder risk score by about 5%, about 10%, about 20% or about 30%. In other embodiments, the post-neuromodulation eating disorder risk score is lower than the initial eating disorder risk score by more than 30%. In certain embodiments, the post-neuromodulation eating disorder risk score can be lower than the threshold risk score.

VII. EXPERIMENTAL EXAMPLES

Example 1

This section describes an example of the outcome of renal neuromodulation on human patients. A total of 45 patients (mean age of 58±9 years) diagnosed with essential hypertension were treated with percutaneous, catheter based renal nerve ablation. Treatment included RF energy delivery to the renal artery using a single-electrode Symplicity Flex™ catheter that was commercially available outside the United States from Medtronic plc, of 710 Medtronic Parkway, Minneapolis, MN 55432-5604. In this human trial, a radiotracer dilution method was used to assess overflow of norepinephrine from the kidneys into circulation before and 15-30 days after the procedure in 10 patients. Bilateral renal-nerve ablation resulted in a marked reduction in mean norepinephrine spillover from both kidneys: 47% (95% confidence interval) one month after treatment.

In a similar human trial where bilateral renal nerve ablation was performed in 70 patients, whole-body norepinephrine levels (i.e., a measure of "total" sympathetic activity), fell by nearly 50% after renal nerve ablation and measurement of muscle sympathetic nerve activity showed a drop of 66% over 6 months, further supporting the conclusion that total sympathetic dive was reduced by the renal denervation procedure in this patient group.

Example 2

Example 2 describes the outcome of catheter-based renal neuromodulation on human patients diagnosed with hypertension. Patients selected having a baseline systolic blood pressure of 160 mm Hg or more (≥150 mm Hg for patients with type 2 diabetes) and taking three or more antihypertensive drugs, were randomly allocated into two groups: 51 assessed in a control group (antihypertensive drugs only) and 49 assessed in a treated group (undergone renal neuromodulation and antihypertensive drugs).

Patients in both groups were assessed at 6 months. Office-based blood pressure measurements in the treated group were reduced by 32/12 mm Hg (SD 23/11, baseline of 178/96 mm Hg, p<0.0001), whereas they did not differ from baseline in the control group (change of 1/0 mm Hg, baseline of 178/97 mm Hg, p=0.77 systolic and p=0.83 diastolic). Between-group differences in blood pressure at 6 months were 33/11 mm Hg (p<0.0001). At 6 months, 41 (84%) of 49 patients who underwent renal neuromodulation had a reduction in systolic blood pressure of 10 mm Hg or more, compared with 18 (35%) of 51 control patients (p<0.0001).

Example 3

Example 3 describes the outcome of catheter-based renal neuromodulation on animal subjects in an additional experiment. In this example (and referring to FIGS. 8A and 8B), studies using the pig model were performed using a multi-electrode Symplicity Spyral™ catheter or a single-electrode Symplicity Flex™ catheter along with a Symplicity G3™ generator. The catheters and generator were commercially available from Medtronic plc in more than 50 countries outside the United States. The catheters were used in these cohorts of animals (n=66) to create multiple RF ablations in the renal vasculature. Cortical axon density in the renal cortex (FIG. 8A) and renal cortical norepinephrine (NE) concentration (FIG. 8B) were used as markers to measure procedural efficacy.

As shown in FIG. 8A, cortical axon area (per mm$^2$) dropped approximately greater than 54% between a control group (n=64) and treated groups of pigs (n=66) undergoing treatment. For pigs undergoing treatment with the Symplicity Flex™ catheter (n=54), an average of 4.1 lesions were formed in each animal. These pigs demonstrated a 56.9% increase in non-functional axonal area along the renal artery, and a 68% decrease in cortical axon area as compared with the control group. For pigs undergoing treatment with the Symplicity Spyral™ catheter (n=12), an average of 4.0 lesions were formed in each animal. The pigs undergoing treatment with the Symplicity Spyral™ catheter demonstrated a 47.3% increase in non-functional area along the renal artery, and a 54% decrease in cortical axon area relative to the control group. Without being bound by theory, it is believed that the loss of cortical axons is a likely consequence of nerve atrophy distal to the ablation sites.

Figure 8B:
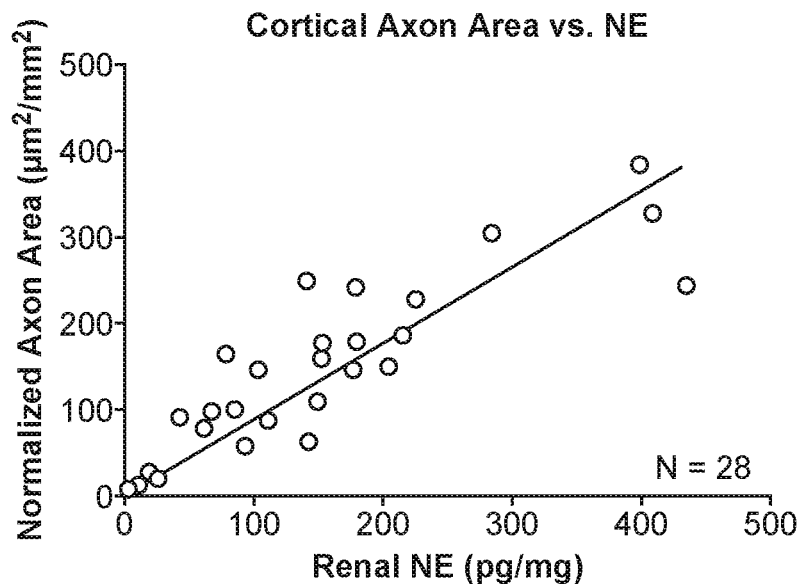
FIG. 8B is a series of graphs illustrating the response correlation between normalized cortical axon area vs. norepinephrine concentration and norepinephrine concentration vs. extent of nerve ablation along the artery of the animal subjects of FIG. 8A.
Figure 8B:
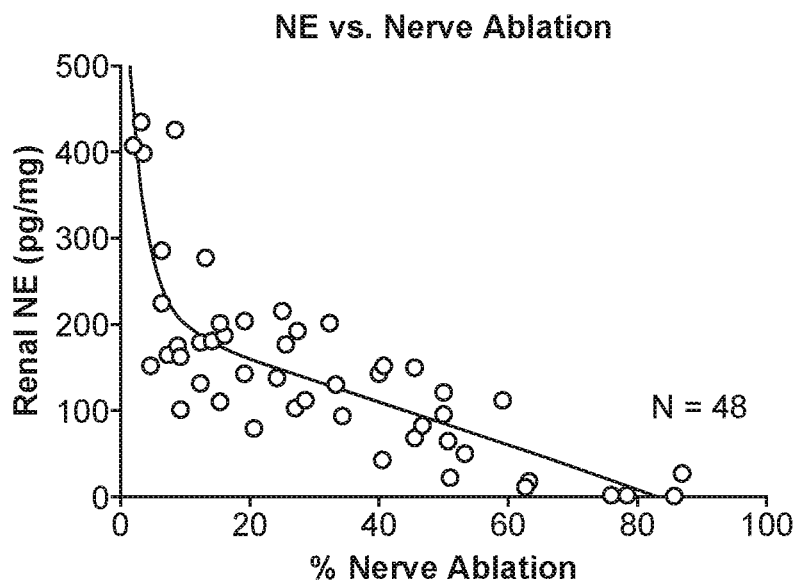

FIG. 8B includes (a) a graph of normalized cortical axon area vs. renal NE concentration, and (b) a graph of renal NE concentration vs. extent (%) of nerve ablation. Referring to the table of FIG. 10A and the two graphs of FIG. 8B together, cortical axon area correlates directly with renal NE. In particular, pigs undergoing treatment with the Symplicity Flex™ catheter exhibited a 65% decrease in mean NE level compared with the pigs in the control group. The pigs treated with the Symplicity Spyral™ catheter exhibited a 68% decrease in mean NE level compared with the pigs in the control group. This is further shown by the first graph of FIG. 8B, which demonstrates that a decrease in cortical axon area correlates with a decrease in NE levels. Referring to the second graph of FIG. 8B, renal NE decrease is non-linear with increased loss of nerve viability along the artery (further extent (%) of nerve ablation). These findings suggest that catheter-based renal neuromodulation exhibits a relatively consistent impact on sympathetic nerve function and viability, and further suggest that neuromodulation of SNS fibers innervating a target tissue and/or organ (such as the kidney) result in a significant decrease in local NE concentration.

Example 4

Example 4 describes an example of the outcome of renal neuromodulation on human patients. Markers of cardiovascular inflammation and remodeling were assessed (Dörr, O., et al., *Clin Res Cardiol*, 2015, 104: 175-184). A total of 60 patients (mean age of 67.9±9.6 years) diagnosed with resistant arterial hypertension were treated with percutaneous, catheter-based renal sympathetic denervation. Treatment included RF energy delivery to the renal artery using a Symplicity® catheter system commercially available outside the United States from Medtronic plc. In this human trial, a therapeutic response was defined as a systolic blood pressure (BP) reduction of >10 mmHg in the office blood pressure measurement 6 months after renal denervation. Of the 60 patients, 49 patients (82%) were classified as responders with a mean systolic BP reduction of >10 mmHg. Venous blood samples for determination of biomarkers of inflammation (e.g., IL-6, high-sensitive C-reactive protein (hsCRP)) and markers of vascular remodeling (matrix metalloproteinases (MMP-2 and MMP-9), tissue inhibitors of matrix metalloproteinases (TIMP-1)) were collected at baseline (prior to renal denervation) and 6 months after renal denervation for all patients.

Collected data from all patients demonstrated that bilateral renal nerve denervation resulted in a significant reduction in mean office systolic BP of 26.4 mmHg (169.3±11.3 mmHg at baseline vs. 142.9±13.8 mmHg at follow-up; p<0.001). The procedure further resulted in a significant reduction in the serum levels of hsCRP (3.6 mg/dL at baseline vs. 1.7 mg/dL at follow-up, p<0.001), and a significant reduction in the pro-inflammatory cytokine IL-6 (4.04 pg/mL at baseline vs. 2.2 pg/mL at follow-up, p<0.001) six months after treatment. Additionally, the procedure resulted in a significant increase in the serum levels of MMP-9 (425.2 ng/mL at base line vs. 574.1 ng/mL at follow-up, p=0.02), and in serum levels of MMP-2 (192.3 ng/mL at baseline vs. 231.3 ng/mL at follow-up, p<0.001). There were no significant changes in TIMP-1 6 months after renal denervation. Notably, of non-responders (e.g., patients with a BP reduction of <10 mmHg), serum levels of hsCRP still decreased (3.2 mg/dL at baseline vs. 2.4 mg/dL at follow-up, p=0.09), and serum levels of IL-6 still decreased (3.1 pg/mL at baseline vs. 2.7 pg/mL at follow-up, p=0.16), although there was a significantly greater beneficial effect of renal denervation on biomarker levels in BP responders when compared with non-responders.

These findings suggest that catheter-based renal neuromodulation exhibits a positive vascular and systemic effect on mediators of inflammation, IL-6 and hsCRP, and inhibitors (MMP-9 and MMP-2) of deleterious cardiovascular remodeling. Low serum levels of MMP-9 and MMP-2 have been found to be essential to damaging vascular remodeling found in essential hypertension and progression of end-organ damage These findings suggest that levels of MMP-9 and MMP-2, which are involved in ECM turnover in different tissues, including the arterial wall, can be elevated post-renal neuromodulation, and, without being bound by theory, are postulated to be beneficial in reversal of damage to the vessels caused by inflammation, cardiovascular disease and/or hypertension. As elevated inflammatory biomarkers, such as IL-6 and CRP, have been proposed as predictors and possible contributors of eating disorder etiology and/or incidence of an eating disorder, these results demonstrate that renal neuromodulation may be useful to reduce a severity of an eating disorder, reverse an eating disorder diagnosis, or reduce a risk associated with the development of an eating disorder in susceptible or at risk patients. In addition to lowering systolic BP in (responsive) hypertensive patients, these findings suggest that renal denervation has a positive effect on biomarkers of inflammation (e.g., IL-6, hsCRP) and cardiovascular remodeling (e.g., MMP-2, MMP-9) separate from and in addition to the effect on blood pressure.

Example 5

Example 5 describes an example of the effects of renal neuromodulation on nocturnal blood pressure using ambulatory 24-hour blood pressure (BP) monitoring in human patients. Elevated blood pressure during the nighttime as well as early morning hours (e.g., elevated morning surge in BP; "MSBP") is associated with an increased risk of cardiovascular events and strokes, and MSBP is associated with sleep disorders independent from "non-dipping" nocturnal blood pressure, with higher morning surges associated with higher levels of sleep disturbance symptoms, including poorer overall sleep quality (FitzGerald, L., et al., *J Hum*

*Hypertens*, 2012, 26: 228-235; Kario, K., et al., *Hypertension*, 2015, 66:1130-1137; Kario, K. and Hamasaki, H., *J Clin Hypertens*, 2015, 17: 682-685). In this example, a total of 576 patients diagnosed with resistant arterial hypertension (e.g., baseline office systolic BP≥160 mm Hg and 24-hour ambulatory systolic BP≥135 mm Hg) were either treated ("RDN treated"; n=382) with bilateral percutaneous, catheter-based renal sympathetic denervation (mean age of 58±11 years) or blindly treated ("blind control"; n=159) with a sham procedure (e.g., renal angiogram) or not treated ("control"; n=19) (Kario, K., et al., *Hypertension*, 2015, 66:1130-1137). Treatment included RF energy delivery to the renal artery using a Symplicity™ catheter system (Medtronic plc). The renal neuromodulation ("RDN") treated group received up to six ablations rotated in 45 degree increments and approximately 5 mm apart for 2 minutes each in both renal arteries. Treatments were delivered from the first distal main renal artery bifurcation to the ostium proximally and were spaced longitudinally and rotationally under fluoroscopic guidance. BP variability, morning ambulatory, nighttime ambulatory and daytime ambulatory systolic BP was measured by 24-hour ambulatory BP monitoring before renal denervation and at 6 months after renal denervation.

In patients with resistant hypertension, renal denervation resulted in significant reduction in ambulatory nighttime and morning BP. For example, mean ambulatory nighttime BP measurements in the RDN treated group were reduced by 6.3±18.2 mm Hg (p<0.001; baseline of 151.5±18.3 mm Hg, p=0.24), whereas they were not significantly reduced (−1.7±19.2 mm Hg; p=0.233) from baseline (149.5±20.1 mm Hg, p=0.24) in the blind control+control group 6 months post-neuromodulation. Further, mean ambulatory morning BP measurements in the RDN treated group were reduced by 7.3±19.6 mm Hg (p<0.001; baseline of 161.2±17.2 mm Hg, p=0.24), whereas they were not significantly reduced (−3.2±21.0 mm Hg; p=0.046) from baseline (160.3±19.2 mm Hg, p=0.579) in the blind control+control group 6 months post-neuromodulation. These findings suggest that patients presenting with an eating disorder and treated with renal neuromodulation will have decreased ambulatory nighttime systolic BP and decreased MSBP which will reduce the patient's likelihood (e.g., lower level of risk) of developing, progressing or worsening cardiovascular disease. These findings further suggest that patients with an eating disorder and treated with renal neuromodulation will improve one or more symptoms relating to the eating disorder.

Example 6

Example 6 describes a method for treating human patients diagnosed with an eating disorder with renal neuromodulation and anticipated outcomes of such treatment. In this example, human patients diagnosed with an eating disorder will be treated with renal denervation and a method of treatment includes modulating nerve tissue surrounding the main renal artery (e.g., locations along the main renal vessel, locations at or near the bifurcation, etc.) and/or modulating nerve tissue surrounding one or more primary branch trunks (e.g., proximal portion of one or more primary branch vessels distal to the bifurcation).

For patients undergoing distal main renal artery treatment, modulating nerve tissue includes forming a plurality of spaced-apart lesions at the distal segment of the renal artery and within a distance of approximately 6 mm proximal to the branch point within the renal artery using the Symplicity Spyral™ catheter, commercially available outside the United States from Medtronic plc. For example, a first (e.g., most distal) lesion can be formed about 5-6 mm proximal from the bifurcation. Other multi-electrode, spiral/helical-shaped catheters for forming multiple lesions along the length of the vessel are also contemplated for these methods. For patients undergoing main artery treatment at a central segment of the main renal artery, the Symplicity Spyral™ catheter can be used to form a plurality of spaced-apart lesions (e.g., about 2 lesions to about 4 lesions) in a spiral/helical pattern along the central segment of the main renal artery. The catheter may also be moved proximally and/or distally to form multiple sets of lesions during a procedure.

For patients undergoing renal branch treatment, modulating nerve tissue includes forming up to about four lesions (e.g., about 2 lesions to about 4 lesions) in one or more primary branch trunks (e.g., from about 1 mm to about 6 mm distal to the primary bifurcation, in regions greater than 2 mm distal to the primary bifurcation). Modulation of nerve tissue at branch trunk treatment sites and/or different combinations of treatment sites within the renal vasculature (e.g., locations along the main renal vessel, locations at or near the bifurcation, etc.) can also be performed using the multi-electrode Symplicity Spyral™ catheter. Other multi-electrode, spiral/helical-shaped catheters having a tighter spiral/helix (e.g., smaller pitch) for forming multiple lesions close in proximity along the length of the vessel are contemplated for these methods.

In a particular example, a method for efficaciously neuromodulating renal nerve tissue in a human patient can include advancing a multi-electrode Symplicity Spyral™ catheter to a first renal artery branch vessel approximately 6 mm distal to the bifurcation. Following retraction of a guidewire and/or straightening sheath, the Symplicity Spyral™ catheter can transform to a spiral/helically-shaped configuration that accommodates the inner diameter of a typical renal artery and/or the branches of the renal artery (e.g., about 2-10 mm), placing the electrodes (e.g., 4 electrodes) in contact with the vessel wall. A first (e.g., most distal) lesion can be formed about 5-6 mm distal to the bifurcation. Following treatment at the first renal artery branch, the catheter can be withdrawn into the main renal vessel and then advanced under fluoroscopy into a second renal artery branch and the treatment procedure can be repeated. Some methods can include treating two branch vessels at the proximal trunk segment of the branch vessel. Other methods can include treating greater than two or all of the primary branch vessels branching from the main renal vessel (e.g., distal to a primary bifurcation). As described above, these methods may also include combining neuromodulation of renal nerve tissue surrounding one or more primary branch trunks with neuromodulation of renal nerve tissue at additional treatment locations (e.g., locations along the main renal vessel, locations at or near the bifurcation, etc.). Other methods can include advancing a multi-electrode Symplicity Spyral™ catheter to a first renal artery branch vessel approximately 10 mm distal to the bifurcation, with a first (e.g., most distal) lesion formed about 9-10 mm distal to the bifurcation.

Physiological biomarkers, such as systemic catecholamines and/or their subsequent degradation products could be measured in either plasma, serum or urine to serve as surrogate markers to measure procedural efficacy such as described in International Patent Application No. PCT/US2015/047568, filed Aug. 28, 2015, and incorporated herein by reference in its entirety.

It is anticipated that treating a human patient diagnosed with an eating disorder or having an increased risk of developing an eating disorder (e.g., a predisposition, having one or more biomarkers suggesting an increased likelihood, genetic/epigenetic factors, etc.) or having one or more measurable risk factors predictive for the development of an eating disorder, with renal neuromodulation, at one or more of the described treatment locations, will inhibit sympathetic neural activity in the renal nerve in a manner that reduces a central sympathetic drive (e.g., as correlated with whole body norepinephrine spillover and/or renal norepinephrine spillover) by greater than about 20%, about 30%, about 40%, about 50% or greater than about 60% in about 1 month, in about 3 months, in about 6 months or in about 12 months, or in another embodiment, in about 3 months to about 12 months, after renal neuromodulation treatment. Reduction in central sympathetic drive is anticipated to result in a therapeutically beneficial improvement in one or more measurable physiological parameters corresponding to an incidence of an eating disorder, and/or a severity of an eating disorder in the patient.

Example 7

Example 7 describes a method for determining human patients who have a calculated risk score for determining an eating disorder status (e.g., diagnosis) at or above a threshold eating disorder risk score and treating such patients with targeted sympathetic neuromodulation of renal SNS neural fibers innervating the kidney. In this example, human patients having a calculated eating disorder risk score meeting or exceeding a threshold eating disorder risk score will be treated with renal neuromodulation to improve the patient's eating disorder risk score and/or lower the patient's eating disorder risk score (e.g., in a manner that improves the patient's eating disorder status, reverses the patient's eating disorder diagnosis, and/or improves one or more symptoms or contributing factors associated with the eating disorder in the patient).

Patients presenting one or more risk factors or indicators predictive for or indicative of an eating disorder will be assessed for other possible risk factors and an eating disorder risk score will be calculated. In this example, a patient will fill out a questionnaire or otherwise have an attending physician assess risk factors. An eating disorder risk score calculator based on risk factor data to determine a probability or likelihood of eating disorder status (e.g., diagnosis) in an individual is shown in FIG. 9. The eating disorder risk score calculator shown in FIG. 9 is derived from data provided in the EDE-Q study to develop a model of a technique to assess duration and/or frequency of eating disorder symptoms and screen the patient for risk factors and indicators of an eating disorder to determine a likelihood and/or severity of an eating disorder diagnosis.

Referring to the eating disorder risk score calculator shown in FIG. 9, a patient will be queried and assessed for core eating disorder indicators (e.g., deliberately trying to limit the amount of food eaten (e.g., to influence one's shape or weight), having gone for long periods of time (e.g., 8 waking hours or more) without eating, trying to exclude from diet any liked foods, trying to follow definite rules regarding eating (e.g., calorie limit) in order to influence body shape or weight, having a definite desire to have an empty stomach with the aim of influencing shape or weight, having a definite desire to have a totally flat stomach, thinking about food and eating or calories making it difficult to concentrate on previously interesting things (e.g., work, conversation, reading, etc.), thinking about shape or weight making it difficult to concentrate on interesting things, having a definite fear of losing control over eating, having a definite fear of gaining weight, having felt fat, having a strong desire to lose weight, etc.). In addition to these twelve clinical indicators, the patient may also be examined and/or tested by a physician for determination of other physiological variables pertaining to the SNS such as, for example, heart rate variability, heart rate reactions to stress, whole body MSNA levels (FIG. 9), and systolic blood pressure (e.g., daytime, nocturnal and morning surge) (not shown in FIG. 9). In this example, the input to the calculator will yield both a patient-specific eating disorder risk score as well as an indication as to whether RDN treatment is recommended. In this example, the threshold eating disorder risk score is 26. An indication of RDN recommendation may be based on whether the patient's eating disorder risk score is at or above the threshold eating disorder risk score, either alone or in combination with one or more physician-administered tests assessing SNS activity or systolic blood pressure level.

As illustrated in FIG. 9, a hypothetical patient reports experiencing 2 eating disorder indicators every day, 1 eating disorder indicator 23-27 days, 3 eating disorder indicators 16-22 days, 1 eating disorder indicators 13-15 days, 3 eating disorder indicators 1-3 days, and indicated that 2 eating disorder indicators were not experienced (e.g., over the past 28 days, 4 weeks). A physician-administered SNS test assessing heart rate variability indicated the patient's SDNN intervals were less than the 50 ms threshold, and a test for baroreflex indicated that the baroreceptor sensitivity was less than 1.74 ms/mmHg; however the patient did not exceed threshold levels in heart rate reactions to stress, and whole body MSNA levels. The hypothetical patient's eating disorder risk score of 35 exceeds the threshold level determination (e.g., greater than 25) for an eating disorder diagnosis. In this example, the eating disorder risk score together with meeting at least one SNS threshold, qualifies the hypothetical patient as a candidate for receiving RDN treatment. In another example, the hypothetical patient is a candidate for receiving RDN treatment with or without the additional SNS tests (or ascertaining a systolic blood pressure for the patient). Following bilateral renal neuromodulation treatment, the hypothetical patient may have improvement in one or more measurable risk factors (e.g., heart rate variability, severity or frequency of anxiety symptoms, nocturnal and/or morning surge blood pressure, etc.), and/or reported risk factors pertaining to core eating disorder symptoms (e.g., intense fear of gaining weight or becoming fat, behaviors that interfere with weight gain (e.g., calorie restriction, purging, use of laxatives, etc.), disturbance in the way one sees body weight or shape, eating large amount of food in a discrete amount of time (e.g., within a 2 hour period), sense of lack of control over eating, eating until uncomfortably full, eating large amounts of food when not feeling physically hungry, recurrent compensatory behavior to prevent weight gain (e.g., self-induced vomiting, misuse of laxatives, diuretics, or medications), fasting, excessive exercise, feeling ashamed or disgusted with oneself, or depressed, etc.), that improves the patient's eating disorder risk score, and in some cases, to levels below the threshold eating disorder risk score level(s).

VIII. FURTHER EXAMPLES

1. In a normotensive patient diagnosed with an eating disorder, a method comprising:

intravascularly positioning a neuromodulation assembly within a renal blood vessel of the patient and adjacent to a renal nerve of the patient; and at least partially inhibiting sympathetic neural activity in the renal nerve of the patient via the neuromodulation assembly, wherein at least partially inhibiting sympathetic neural activity results in a therapeutically beneficial improvement in a measurable parameter associated with the eating disorder of the patient.

2. The method of example 1 wherein the patient is diagnosed with binge eating or bulimia nervosa, and wherein at least partially inhibiting sympathetic neural activity in the patient in a manner that results in a therapeutically beneficial improvement in a measurable parameter associated with the eating disorder comprises one or more of reducing a frequency of binge eating episodes and reducing a frequency of purging following eating in the patient.

3. The method of example 1 or example 2 wherein the patient is diagnosed with one or more of binge eating disorder, bulimia nervosa, anorexia nervosa, pica disorder and rumination disorder.

4. The method of any one of examples 1-3 wherein reducing sympathetic neural activity in the patient in a manner that results in a therapeutically beneficial improvement in a measurable parameter associated with the eating disorder comprises reducing a morning surge blood pressure and/or a nocturnal blood pressure in the patient.

5. The method of example 1 wherein the patient is diagnosed with anorexia nervosa, wherein reducing sympathetic neural activity in the patient in a manner that results in a therapeutically beneficial improvement in a measurable parameter associated with the eating disorder comprises increasing the amount of food eaten by the patient.

6. The method of any one of examples 1-5 wherein reducing sympathetic neural activity in the patient further comprises improving one or more eating disorder symptoms in the patient as reported on an eating disorder screening tool.

7. The method of example 6 wherein improving one or more eating disorder symptoms in the patient includes reducing a level of eating disorder symptoms and/or a number of eating disorder symptoms.

8. The method of example 6 or example 7 wherein improving one or more eating disorder symptoms in the patient includes reducing a level of eating disorder symptoms in the patient by at least about 5%, at least about 10%, at least about 20% or at least about 40%.

9. The method of example 6 or example 7 wherein improving one or more eating disorder symptoms in the patient includes reducing a number of eating disorder symptoms in the patient by at least about 5%, at least about 10%, at least about 20% or at least about 40% within about three months to about 12 months after at least partially inhibiting sympathetic neural activity in the patient by delivering energy to the renal nerve.

10. The method of any one of examples 1-9 wherein the patient is further diagnosed with depression or an anxiety disorder.

11. The method of any one of examples 1-10 wherein the patient is between the ages of 18 and 45, between the ages of 18 and 30, between the ages of 20 and 40, or between the ages of 20 and 35.

12. The method of any one of examples 1-10 wherein the patient is between the ages of 35 and 65, between the ages of 45 and 65, between the ages of 50 and 70, or the patient is at least 35 years old.

13. The method of any one of examples 1-12 wherein at least partially inhibiting sympathetic neural activity in the patient further comprises reducing an incidence of stroke or cardiovascular disease in the patient.

14. The method of any one of examples 1-12 wherein the patient has a history of cardiovascular disease or stroke, and wherein at least partially inhibiting sympathetic neural activity in the patient further comprises reducing an incidence of a future cardiovascular event or stroke.

15. The method of example 1 wherein at least partially inhibiting sympathetic neural activity in the patient in a manner that results in a therapeutically beneficial improvement in a measurable parameter associated with the eating disorder comprises improving a patient's eating disorder risk score on an eating disorder screening tool.

16. The method of any one of examples 1-15 wherein at least partially inhibiting sympathetic neural activity in the patient in a manner that results in a therapeutically beneficial improvement in a measurable parameter associated with the eating disorder includes one or more of:
  increasing a heart rate variability of the patient;
  increasing baroreceptor sensitivity in the patient;
  reducing a morning surge blood pressure in the patient;
  reducing a plasma cortisol level in the patient;
  reducing a level of glucocorticoid resistance in the patient; and
  reducing a level of an inflammatory biomarker in the patient.

17. The method of example 16 wherein the inflammatory biomarker is at least one of interleukin-6, interleukin-8, tumor necrosis factor-alpha, and C-reactive protein.

18. The method of any one of examples 1-17 wherein reducing sympathetic neural activity in the renal nerve further reduces muscle sympathetic nerve activity (MSNA) in the patient.

19. The method of any one of examples 1-18 wherein reducing sympathetic neural activity in the renal nerve further reduces whole body norepinephrine spillover in the patient.

20. The method of example 19 wherein the whole body norepinephrine spillover is reduced by at least about 20% in about one month or reduced by greater than about 40% in about three months to about 12 months after reducing sympathetic neural activity in the renal nerve.

21. The method of example 1, further comprising delivering energy to renal perivascular adipose tissue adjacent to the renal blood vessel of the patient via the neuromodulation assembly to reduce norepinephrine spillover to plasma.

22. The method of any one of examples 1-21 wherein the patient is currently administered one or more pharmaceutical drugs for the eating disorder, and wherein at least partially inhibiting sympathetic neural activity in the patient in a manner that results in a therapeutically beneficial improvement in a measurable parameter associated with the eating disorder comprises reducing at least one of a number of or a measured dosage of pharmaceutical drugs administered to the patient for the eating disorder.

23. The method of example 22 wherein the pharmaceutical drugs include one or more of an anti-anxiety drug, antidepressant, an anti-psychotic drug, an insomnia drug, an obesity drug or an anti-inflammatory drug.

24. In a human patient, a method of reducing a risk of the patient developing an eating disorder, the method comprising:
  intravascularly positioning a catheter carrying a neuromodulation assembly adjacent to a renal sympathetic nerve of the patient;

delivering energy to the renal sympathetic nerve via the neuromodulation assembly to attenuate neural traffic along the renal sympathetic nerve; and removing the catheter and neuromodulation assembly from the patient after treatment, wherein attenuating neural traffic along the renal sympathetic nerve reduces a risk of the patient developing the eating disorder.

25. The method of example 24 wherein the risk of developing the eating disorder is calculated using an eating disorder screening tool, and wherein a post-neuromodulation eating disorder risk score for the patient, as calculated by the eating disorder screening tool, is lower than an initial eating disorder risk score.

26. The method of example 24 or example 25 wherein attenuating neural traffic along the renal sympathetic nerve further results in one or more of:
increasing heart rate variability in the patient;
increasing baroreceptor sensitivity in the patient;
reducing a level of glucocorticoid resistance in the patient;
reducing a cortisol level in the patient;
reducing a systolic blood pressure of the patient;
reducing a morning surge blood pressure in the patient;
reducing a nocturnal blood pressure in the patient;
reducing muscle sympathetic nerve activity (MSNA) in the patient;
reducing a plasma or urine norepinephrine level in the patient; and
reducing a level of an inflammatory biomarker in the patient.

27. The method of example 26 wherein the inflammatory biomarker is at least one of interleukin-6, interleukin-8, tumor necrosis factor-alpha, and C-reactive protein.

28. The method of any one of examples 24-27 wherein the patient has a personal or family history of eating disorders, anxiety disorders and/or depression, and wherein attenuating neural traffic along the renal sympathetic nerve reduces an incident of a future eating disorder in the patient.

29. The method of any one of examples 24-28 wherein the patient is currently experiencing an adverse life circumstance and is diagnosed with one or more of low heart rate variability, elevated plasma or urine catecholamine levels, elevated systolic blood pressure, elevated morning surge in blood pressure, non-dipping nocturnal blood pressure, low neuropeptide Y level, elevated plasma cortisol level, glucocorticoid resistance, elevated cortisol awakening rise (CAR), reduced baroreceptor sensitivity, and elevated level of an inflammatory biomarker.

30. The method of any one of examples 24-29 wherein the patient has a polymorphism in at least one of the genes encoding for FK506-binding protein 5 (FKBP5 gene), glucocorticoid receptor (NR3C1 gene), cortisol releasing hormone receptor-1 (CRHR1 gene), tumor necrosis factor (TNF)-alpha, that provide an increased likelihood of developing the eating disorder.

31. The method of any one of examples 24-30 wherein the patient is diagnosed with cardiovascular disease.

32. The method of any one of examples 24-31 wherein the patient has a history of stroke.

33. The method of any of examples 24-32 wherein the patient has one or more eating disorder risk factors selected from the group consisting of increased substance abuse, hypertension, elevated norepinephrine whole body spillover, exposure to multiple traumatic events, female gender, family history of mental disorder, adverse childhood experience and diagnosed with narcissistic personality disorder.

34. The method of any one of examples 24-33 wherein attenuating neural traffic along the renal sympathetic nerve comprises at least partially ablating the renal sympathetic nerve.

35. The method of any one of examples 24-33 wherein attenuating neural traffic along the renal sympathetic nerve comprises at least partially disrupting communication along the renal sympathetic nerve.

36. The method of any one of examples 24-33 wherein attenuating neural traffic along the renal sympathetic nerve comprises irreversibly disrupting communication along the renal sympathetic nerve.

37. The method of any one of examples 24-33 wherein attenuating neural traffic along the renal sympathetic nerve comprises delivering an energy field to the renal sympathetic nerve via the neuromodulation assembly.

38. The method of example 37 wherein delivering an energy field to the renal sympathetic nerve comprises delivering at least one of radio frequency energy, ultrasound energy, high intensity ultrasound energy, laser energy, and microwave energy via the neuromodulation assembly.

39. The method of any one of examples 24-38 wherein the patient is diagnosed with prehypertension or hypertension, and wherein attenuating neural traffic along the renal sympathetic nerve further reduces whole body norepinephrine spillover in the patient in a manner that reduces the risk of the patient developing the eating disorder.

40. A method for improving a patient's risk score corresponding to an eating disorder status of the patient, the method comprising:
intravascularly positioning a catheter carrying a neuromodulation assembly within a renal blood vessel and adjacent to a renal sympathetic nerve in the patient;
delivering energy to the renal sympathetic nerve via the neuromodulation assembly to attenuate neural traffic along the renal sympathetic nerve; and
removing the catheter and neuromodulation assembly from the patient after treatment,
wherein attenuating neural traffic along the renal sympathetic nerve results in improving the patient's risk score corresponding to the eating disorder status of the patient.

41. The method of example 40 wherein improving the patient's risk score corresponding to the eating disorder status of the patient includes one or more of improving eating disorder symptoms, reducing the patient's anxiety level, reducing a level of systemic inflammation in the patient, and improving a patient's body mass index.

42. The method of example 40 or example 41 wherein the patient is diagnosed with pre-hypertension or hypertension, and wherein improving the patient's risk score corresponding to the eating disorder status of the patient includes reducing the patient's blood pressure.

43. The method of any one of examples 40-42 wherein a patient's risk score corresponding to the eating disorder status of the patient is reduced by at least about 10%, at least about 15%, at least about 20%, at least about 30% or at least about 40%.

44. The method of any one of examples 40-43 wherein the patient's risk score is calculated using an eating disorder screening tool, and wherein a post-neuromodulation eating disorder risk score, as calculated by the eating disorder screening tool, is lower than an initial eating disorder risk score.

45. The method of example 44, wherein the eating disorder screening tool includes an Eating Disorder Examination Questionnaire (EDE-Q) for assessing an eating disorder severity.

46. A method for improving an eating disorder risk score for a human patient diagnosed with an eating disorder, the method comprising performing a renal neuromodulation procedure in the patient diagnosed with the eating disorder, wherein a post-neuromodulation risk score is lower than an initial risk score of the patient diagnosed with the eating disorder.

47. The method of example 46 wherein the post-neuromodulation risk score is lower than the initial risk score by about 5%, about 10%, about 20% or about 30%.

48. The method of example 46 or example 47 wherein the initial risk score indicates the patient is at risk of having the eating disorder if the initial risk score is greater than a threshold risk score.

49. The method of any one of examples 46-48 wherein the initial risk score and the post-neuromodulation risk score are determined using an eating disorder screening tool for determining a severity of the eating disorder of the patient.

50. The method of any one of examples 46-49 wherein the initial risk score and the post-neuromodulation risk score are based upon one or more factors comprising a psychological evaluation, type and/or severity of eating disorder symptoms, duration of eating disorder symptoms experienced by the patient, number of instances of trauma exposure, and symptoms associated with a mood disorder.

51. A method for managing an eating disorder in a normotensive human patient, the method comprising:
    transluminally positioning an energy delivery element of a catheter within a renal blood vessel of the patient and adjacent to renal sympathetic neural fibers in the patient; and
    at least partially ablating the renal sympathetic neural fibers via the energy delivery element,
    wherein at least partially ablating the renal sympathetic neural fibers results in a therapeutically beneficial improvement in a measurable parameter associated with the eating of the patient.

52. The method of example 51 wherein the patient is diagnosed with binge eating or bulimia nervosa, wherein at least partially ablating the renal sympathetic neural fibers in the patient in a manner that results in a therapeutically beneficial improvement in a measurable parameter associated with the eating disorder comprises one or more of reducing a frequency of binge eating episodes and reducing a frequency of purging following eating in the patient.

53. The method of example 51 or 52 wherein at least partially ablating the renal sympathetic neural fibers in the patient in a manner that results in a therapeutically beneficial improvement in a measurable parameter associated with the eating disorder comprises at least one of reducing a nocturnal blood pressure and reducing a morning surge in blood pressure in the patient.

54. The method of any one of examples 51-53 wherein at least partially ablating the renal sympathetic neural fibers in the patient in a manner that results in a therapeutically beneficial improvement in a measurable parameter associated with the eating disorder comprises improving one or more eating disorder symptoms in the patient.

55. The method of any one of examples 51-54 wherein at least partially ablating the renal sympathetic neural fibers further results in reducing an incidence of one or more of hypertension, cardiovascular disease, obesity, diabetes, insulin resistance, systemic inflammation, kidney disease, stroke and dementia in the patient.

56. The method of any one of examples 51-55 wherein at least partially ablating the renal sympathetic neural fibers further results in a therapeutically beneficial improvement in a measurable physiological parameter associated with a comorbid condition in the patient.

57. The method of example 56 wherein the comorbid condition is one or more of depression, anxiety disorder, cancer, cardiovascular disease, obesity, metabolic disorder, systemic inflammation, dementia and infertility.

58. The method of any one of examples 51-57, further comprising administering one or more pharmaceutical drugs to the patient, wherein the pharmaceutical drugs are selected from the group consisting of anti-insomnia drugs, anti-anxiety drugs, antidepressants, anti-hypertension drugs, anti-obesity drugs, and anti-inflammatory drugs.

59. The method of any one of examples 51-58 wherein at least partially ablating the renal sympathetic neural fibers of the patient via the energy delivery element comprises delivering a thermal electric field to the sympathetic neural fibers via at least one electrode.

60. A method for treating a patient that can answer affirmatively, if asked, to at least two of the following statements:
    in the past four weeks and at least most of the time—
        a) you deliberately try limiting the amount of food you eat,
        b) you have gone for long periods of time without eating anything,
        c) you have tried to exclude from your diet foods that you like,
        d) you have a definite desire to have an empty stomach,
        e) you have a definite desire to have a totally flat stomach,
        f) thinking about food, eating or calories makes it difficult concentrate,
        g) thinking about shape or weight of your body makes it difficult to concentrate,
        h) you have a definite fear of losing control over eating,
        i) you have a definite fear that you might gain weight,
        j) you have felt fat, and
        k) you have a strong desire to lose weight,
    the method comprising:
        intravascularly positioning a neuromodulation assembly within a renal blood vessel of the patient and adjacent to a renal nerve of the patient; and
        at least partially inhibiting sympathetic neural activity in the renal nerve of the patient via the neuromodulation assembly,
        wherein at least partially inhibiting sympathetic neural activity results in a therapeutically beneficial improvement in the patient's response to one or more of statements a-k.

IX. CONCLUSION

The above detailed descriptions of embodiments of the technology and methodology are not intended to be exhaustive or to limit the technology to the precise forms disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method comprising:
   determining a baseline measurement of a measurable parameter associated with an eating disorder of a patient, wherein the patient is diagnosed with the eating disorder, and wherein the measurable parameter comprises at least one of a norepinephrine content, a heart rate, a heart rate variability, a morning surge blood pressure, a nocturnal blood pressure level, a systolic blood pressure, a blood pressure variability, baroreceptor sensitivity, skin conductance, or an inflammatory biomarker levels;
   at least partially ablating a renal nerve using a neuromodulation assembly positioned within a renal blood vessel of the patient;
   determining a post-neuromodulation measurement of the measurable parameter; and
   comparing the post-neuromodulation measurement and the baseline measurement to determine a change in the measurable parameter,
   wherein the change in the measurable parameter indicates a therapeutically beneficial improvement in at least one of a frequency of a symptom of the eating disorder, a level of severity of the eating disorder, or a number, type and/or duration of an eating disorder indication.

2. The method of claim 1, wherein the therapeutically beneficial improvement in the frequency of the symptom of the eating disorder indicates a reduction in the symptom of the eating disorder.

3. The method of claim 1, wherein the patient is diagnosed with binge eating or bulimia nervosa, and wherein the change in the measurable parameter indicates one or more of a reduced frequency of binge eating episodes or a reduced frequency of purging following eating by the patient following treatment.

4. The method of claim 1, wherein the patient is diagnosed with anorexia nervosa, and wherein the change in the measurable parameter indicates an amount of food eaten by the patient is increased following treatment.

5. The method of claim 1, wherein the patient is normotensive.

6. The method of claim 1, wherein determining the baseline measurement of the measurable parameter comprises determining the baseline measurement of the measurable parameter before at least partially ablating the renal nerve.

7. The method of claim 1, wherein determining the baseline measurement of the measurable parameter comprises determining the baseline measurement based on a population of subjects.

8. The method of claim 1, further comprising delivering energy to renal perivascular adipose tissue adjacent to the renal blood vessel of the patient via the neuromodulation assembly to reduce norepinephrine spillover.

9. The method of claim 1, wherein at least partially ablating the renal nerve comprises delivering electrical energy, ultrasound energy, magnetic energy, or optical energy via the neuromodulation assembly positioned within the renal blood vessel.

10. The method of claim 1, wherein at least partially ablating the renal nerve comprises delivering a chemical via the neuromodulation assembly positioned within the renal blood vessel.

11. The method of claim 1, wherein at least partially ablating the renal nerve comprises thermally inducing modulation of the renal nerve via the neuromodulation assembly positioned within the renal blood vessel.

12. A method for treating a patient diagnosed with an eating disorder, the method comprising:
    determining a baseline measurement of a measurable parameter associated with an eating disorder of a patient, wherein the patient is diagnosed with the eating disorder, and wherein the measurable parameter comprises at least one of a norepinephrine content, a heart rate, a heart rate variability, a morning surge blood pressure, a nocturnal blood pressure level, a systolic blood pressure, a blood pressure variability, baroreceptor sensitivity, skin conductance, or an inflammatory biomarker levels;
    delivering neuromodulation therapy to the patient via a neuromodulation assembly positioned within a renal blood vessel of the patient;
    determining a post-neuromodulation measurement of the measurable parameter;
    comparing the post-neuromodulation measurement and the baseline measurement to determine a change in the measurable parameter, wherein the change in the measurable parameter indicates a therapeutically beneficial improvement in at least one of a frequency of a symptom of the eating disorder, a level of severity of the eating disorder, or a number, type and/or duration of an eating disorder indication;
    based on the change in the measurable parameter, delivering further neuromodulation therapy to the patient via the neuromodulation assembly positioned within the renal blood vessel of the patient.

13. The method of claim 12, wherein the improvement in the frequency of the symptom of the eating disorder indicates a reduction in a symptom of the eating disorder.

14. The method of claim 12, wherein the patient is diagnosed with binge eating or bulimia nervosa, and wherein the change in the measurable parameter indicates one or more of a reduced frequency of binge eating episodes or a reduced frequency of purging following eating by the patient following treatment.

15. The method of claim 12, wherein the patient is diagnosed with anorexia nervosa, and wherein the change in the measurable parameter indicates an amount of food eaten by the patient is increased following treatment.

16. A method comprising:
    determining a baseline measurement of a measurable parameter associated with an eating disorder of a patient, wherein the patient is diagnosed with the eating disorder, and wherein the measurable parameter comprises at least one of skin conductance, a glucocorticoid level, glucocorticoid resistance, a cardiac autonomic regulation level, a Neuropeptide Y level, a corticotropin-releasing hormone level, an inflammatory biomarker levels, or body mass index;
    at least partially ablating a renal nerve using a neuromodulation assembly positioned within a renal blood vessel of the patient;
    determining a post-neuromodulation measurement of the measurable parameter; and
    comparing the post-neuromodulation measurement and the baseline measurement to determine a change in the measurable parameter,
    wherein the change in the measurable parameter indicates an improvement in the measurable parameter associated with the eating disorder of the patient.

17. The method of claim 16, wherein the improvement in the measurable parameter indicates a reduction in a symptom of the eating disorder.

18. The method of claim 16, wherein the patient is diagnosed with binge eating or bulimia nervosa, and wherein the change in the measurable parameter indicates one or more of a reduced frequency of binge eating episodes or a reduced frequency of purging following eating by the patient following treatment.

19. The method of claim 16, wherein the patient is diagnosed with anorexia nervosa, and wherein the change in the measurable parameter indicates an amount of food eaten by the patient is increased following treatment.

20. The method of claim 1, wherein the change in the measurable parameter associated with the eating disorder of the patient comprises at least one of a decreased heart rate, an increased heart rate variability, a reduced morning surge blood pressure, a decreased nocturnal blood pressure, a decreased systolic blood pressure, an increased blood pressure variability, an increased baroreceptor sensitivity, a decreased skin conductance, or decreased inflammatory biomarker levels.

* * * * *